(12) United States Patent
Bhatta et al.

(10) Patent No.: US 11,345,760 B2
(45) Date of Patent: May 31, 2022

(54) MULTISPECIFIC ANTIBODY CONSTRUCTS

(71) Applicant: UCB BIOPHARMA SRL, Brussels (BE)

(72) Inventors: Pallavi Bhatta, Slough (GB); Emma Dave, Slough (GB); Sam Philip Heywood, Slough (GB); David Paul Humphreys, Slough (GB)

(73) Assignee: UCB BIOPHARMA SRL, Brussels (BE)

( * ) Notice: Subject to any disclaimer, the term of this patent is extended or adjusted under 35 U.S.C. 154(b) by 0 days.

(21) Appl. No.: 15/321,055

(22) PCT Filed: Jun. 25, 2015

(86) PCT No.: PCT/EP2015/064409
§ 371 (c)(1),
(2) Date: Dec. 21, 2016

(87) PCT Pub. No.: WO2015/197772
PCT Pub. Date: Dec. 30, 2015

(65) Prior Publication Data
US 2017/0204200 A1    Jul. 20, 2017

(30) Foreign Application Priority Data
Jun. 25, 2014 (GB) .................................. 1411320

(51) Int. Cl.
*C07K 16/46* (2006.01)

(52) U.S. Cl.
CPC ........ *C07K 16/468* (2013.01); *C07K 2317/31* (2013.01); *C07K 2317/55* (2013.01); *C07K 2317/622* (2013.01); *C07K 2317/624* (2013.01); *C07K 2317/64* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,741,900 | A | 5/1988 | Alvarez et al. |
| 5,219,996 | A | 6/1993 | Bodmer et al. |
| 5,223,409 | A | 6/1993 | Ladner et al. |
| 5,403,484 | A | 4/1995 | Ladner et al. |
| 5,427,908 | A | 6/1995 | Dower et al. |
| 5,516,637 | A | 5/1996 | Huang et al. |
| 5,545,806 | A | 8/1996 | Lonberg et al. |
| 5,569,825 | A | 10/1996 | Lonberg et al. |
| 5,571,698 | A | 11/1996 | Ladner et al. |
| 5,580,717 | A | 12/1996 | Dower et al. |
| 5,585,089 | A | 12/1996 | Queen et al. |
| 5,625,126 | A | 4/1997 | Lonberg et al. |
| 5,633,425 | A | 5/1997 | Lonberg et al. |
| 5,658,727 | A | 8/1997 | Barbas et al. |
| 5,661,016 | A | 8/1997 | Lonberg et al. |
| 5,667,425 | A | 9/1997 | Pineau et al. |
| 5,698,426 | A | 12/1997 | Huse |
| 5,733,743 | A | 3/1998 | Johnson et al. |
| 5,750,753 | A | 5/1998 | Kimae et al. |
| 5,770,429 | A | 6/1998 | Lonberg et al. |
| 5,780,225 | A | 7/1998 | Wigler et al. |
| 5,821,047 | A | 10/1998 | Garrard et al. |
| 5,959,083 | A | 9/1999 | Bosslet et al. |
| 5,969,108 | A | 10/1999 | McCafferty et al. |
| 7,138,103 | B2 | 11/2006 | Goldenberg et al. |
| 8,216,805 | B2 | 7/2012 | Carter et al. |
| 2008/0050370 | A1 | 2/2008 | Glaser et al. |
| 2010/0081796 | A1 | 4/2010 | Brinkmann et al. |
| 2014/0120581 | A1 | 5/2014 | Niwa et al. |

FOREIGN PATENT DOCUMENTS

| | | |
|---|---|---|
| EA | 15992 | 1/2012 |
| EP | 0392745 A2 | 10/1990 |
| EP | 0463151 A1 | 1/1992 |
| EP | 0546073 B1 | 9/1997 |
| EP | 2578230 A1 | 4/2013 |
| EP | 2784092 A2 | 10/2014 |
| JP | 2004-523205 A | 8/2004 |
| JP | 2012-503612 A | 2/2012 |
| JP | 2012-503638 A | 2/2012 |
| RU | 2473362 C2 | 1/2013 |

(Continued)

OTHER PUBLICATIONS

Mertens et al (CBR, 19(1):99-109, 2004).*
Young etal (FEBS, 377:135-139, 1995).*
Wei etal (CO, 35:423-434, 2012).*
Fiege etal (BBA, 1844:2024-2031,2014).*
Reiter et al., Antibody Engineering of Recombinant Fv Immunotoxins for Improved Targeting of Cancer: Disulfide-stabilized Fv Immunotoxins. Clinical Cancer Research. 2:245-252 (1996).
Webber et al., Preparation and Characterization of a Disulfide-Stabilized Fv Fragment of the Anti-Tac Antibody: Comparison with its Single-Chain Analog. Molecular Immunology. 32: 249-258 (1995).
Zhao et al., Stabilization of the Single-Chain Fragment Variable by an Interdomain Disulfide Bond and its Effect on Antibody Affinity. International Journal of Molecular Sciences. 12: 1-11 (2011).

(Continued)

*Primary Examiner* — Brad Duffy
(74) *Attorney, Agent, or Firm* — Marshall, Gerstein & Borun LLP

(57) ABSTRACT

The present disclosure relates to a multi-specific antibody molecule comprising or consisting of: a) a polypeptide chain of formula (I): VH—$CH_1$—X—$V_1$; and b) a polypeptide chain of formula (II): VL-CL-Y—$V_2$ and pharmaceutical formulations comprising, for example for use in treatment. The disclosure also provides polynucleotide sequences encoding said multispecific antibody molecules, vectors comprising the polynucleotides and host cells comprising said vectors and/or polynucleotide sequences. There is a provided a method of expressing a multispecific antibody molecule of the present disclosure from a host cell.

26 Claims, 9 Drawing Sheets
Specification includes a Sequence Listing.

(56) References Cited

FOREIGN PATENT DOCUMENTS

| | | |
|---|---|---|
| WO | WO-1986/001533 A1 | 3/1986 |
| WO | WO-1989/000195 A1 | 1/1989 |
| WO | WO-1989/001476 A1 | 2/1989 |
| WO | WO-1990/002809 A1 | 3/1990 |
| WO | WO-1990/004036 A1 | 4/1990 |
| WO | WO-1991/009967 A1 | 7/1991 |
| WO | WO-1991/010737 A1 | 7/1991 |
| WO | WO-1991/010741 A1 | 7/1991 |
| WO | WO-1992/001047 A1 | 1/1992 |
| WO | WO-1992/002551 A1 | 2/1992 |
| WO | WO-1992/018619 A1 | 10/1992 |
| WO | WO-1992/022583 A2 | 12/1992 |
| WO | WO-1993/006231 A1 | 4/1993 |
| WO | WO-1993/011236 A1 | 6/1993 |
| WO | WO-1994/009131 A1 | 4/1994 |
| WO | WO-1995/015982 A2 | 6/1995 |
| WO | WO-1995/020401 A1 | 8/1995 |
| WO | WO-1997/038102 A1 | 10/1997 |
| WO | WO-1998/020734 A1 | 5/1998 |
| WO | WO-1998/025971 A1 | 6/1998 |
| WO | WO-1999/037791 A1 | 7/1999 |
| WO | WO-1999/064460 A1 | 12/1999 |
| WO | WO-2001/030305 | 5/2001 |
| WO | WO-2001/077342 A1 | 10/2001 |
| WO | WO-2001/090192 A2 | 11/2001 |
| WO | WO-2002/008293 A2 | 1/2002 |
| WO | WO-2003/012069 A2 | 2/2003 |
| WO | WO-2003/031581 A2 | 4/2003 |
| WO | WO-2004/051268 A1 | 6/2004 |
| WO | WO-2004/106377 A1 | 12/2004 |
| WO | WO-2005/003169 A2 | 1/2005 |
| WO | WO-2005/003170 A2 | 1/2005 |
| WO | WO-2005/003171 A2 | 1/2005 |
| WO | WO-2005/017148 A1 | 2/2005 |
| WO | WO-2005/113605 A1 | 12/2005 |
| WO | WO-2005/117984 A2 | 12/2005 |
| WO | WO-2007/095338 A2 | 8/2007 |
| WO | WO-2007/106120 A2 | 9/2007 |
| WO | WO-2007/109254 A2 | 9/2007 |
| WO | WO-2007/146968 A2 | 12/2007 |
| WO | WO-2008/024188 A2 | 2/2008 |
| WO | WO-2008/038024 A1 | 4/2008 |
| WO | WO-2008/094708 A2 | 8/2008 |
| WO | WO-2009/018386 A1 | 2/2009 |
| WO | WO-2009/021754 A2 | 2/2009 |
| WO | WO-2009/023386 A2 | 2/2009 |
| WO | WO-2009/032782 A2 | 3/2009 |
| WO | WO-2009/040562 A1 | 4/2009 |
| WO | WO-2009/068630 A1 | 6/2009 |
| WO | WO-2010/034441 A1 | 4/2010 |
| WO | WO-2010/035012 A1 | 4/2010 |
| WO | WO-2010/112193 A1 | 10/2010 |
| WO | WO-2010/115552 A1 | 10/2010 |
| WO | WO-2010/136172 A1 | 12/2010 |
| WO | WO-2010/145792 A1 | 12/2010 |
| WO | WO-2010/145793 A1 | 12/2010 |
| WO | WO-2011/036460 A1 | 3/2011 |
| WO | WO-2011/138391 A1 | 11/2011 |
| WO | WO-2012/025525 A1 | 3/2012 |
| WO | WO-2012/025530 A1 | 3/2012 |
| WO | WO-2013/049234 A2 | 4/2013 |
| WO | WO-2013/068571 A1 | 5/2013 |
| WO | WO-2013068563 A2 | 5/2013 |
| WO | WO-2013068571 A1 * | 5/2013 | ............ C07K 16/18 |
| WO | WO-2013/163427 A1 | 10/2013 |
| WO | WO-2013163427 A1 * | 10/2013 | ........ C07K 16/1063 |
| WO | WO-2014/096390 A1 | 6/2014 |
| WO | WO-2014/114800 A1 | 7/2014 |
| WO | WO-2014/144722 A2 | 9/2014 |
| WO | WO-2015/150447 A1 | 10/2015 |
| WO | WO-2015/181282 A1 | 12/2015 |
| WO | WO-2016/009029 A1 | 1/2016 |
| WO | WO-2016/009030 A2 | 1/2016 |
| WO | WO-2016/170137 A1 | 10/2016 |

OTHER PUBLICATIONS

Adair et al., Therapeutic Antibodies, *Drug Design Reviews*. 2:209-17 (2005).

Altschul et al., Basic local alignment search tool. *J. Mol. Biol.* 215: 403-10 (1990).

Altschul et al., Gapped BLAST and PSI-BLAST: a new generation of protein database search programs. *Nucl. Acids Res.* 25: 3389-402 (1997).

Ames et al., Conversion of murine Fabs isolated from a combinatorial phage display library to full length immunoglobulins. *J. Immunol. Meth.* 184: 177-86 (1995).

Angal et al., A single amino acid substitution abolishes the heterogeneity of chimeric mouse/human (lgG4) antibody, *Mol. Immunol.* 30:105-108 (1993).

Babcook et al., A novel strategy for generating monoclonal antibodies from single, isolated lymphocytes producing antibodies of defined specificities. *Proc. Natl. Acad. Sci. USA*, 93(15): 7843-8(1996).

Brinkmann et al., A recombinant immunotoxin containing a disulfide-stabilized Fv fragment. *Proc. Natl. Acad. Sci. USA*, 90: 7538-42 (1993).

Brinkmann et al., Phage display of disulfide-stabilized Fv fragments. *J. Immunol. Methods*. 182: 41-50(1995).

Burton et al., Human antibodies from combinatorial libraries. *Adv. Immunol.* 57: 191-280 (1994).

Carter, Bispecific human IgG by design, *J. Immunol. Methods*. 248:7-15 (2001).

Chapman, PEGylated antibodies and antibody fragments for improved therapy: a review. *Adv. Drug Deliv. Rev.* 54: 531-45 (2002).

Cole et al., The EBV-Hybridoma technique and its application to human lung cancer, *Monoclonal Antibodies and Cancer Therapy*. 27:77-96 (1985).

Coloma et al., Design and production of novel tetravalent bispecific antibodies. *Nat. Biotechnol.* 15: 159-63 (1997).

Crameri et al., DNA shuffling of a family of genes from diverse species accelerates directed evolution. *Nature*. 391: 288-91 (1998).

Croasdale et al., Development of tetravalent IgG1 dual targeting IGF-1R-EGFR antibodies with potent tumor inhibition. *Arch. Biochem. Biophys.* 526: 206-18 (2012).

Dubowchik et al., Receptor-mediated and enzyme-dependent targeting of cytotoxic anticancer drugs. *Pharmacol. Ther.* 83: 67-123 (1999).

Fischer et al., Bispecific antibodies: molecules that enable novel therapeutic strategies, *Pathobiology*. 74:3-14 (2007).

Gish et al., Identification of protein coding regions by database similarity search. *Nat. Genet.* 3:266-72 (1993).

Glockshuber et al., A comparison of strategies to stabilize immunoglobulin Fv-fragments. *BiochemistrY*. 29:1362-7 (1990).

Griffin et al., Computer Analysis of Sequence Data, Part 1, Humana Press, New Jersey, (1994).

Harris, Processing of C-terminal lysine and arginine residues of proteins isolated from mammalian cell culture, *J. Chromatogr.* 705:129-34 (1995).

Hellstrom et al., Antibodies for Drug Delivery, *Controlled Drug Delivery*. 2:623-53 (1987).

Holliger et al., Engineered antibody fragments and the rise of single domains, *Nat. Biotechnol*. 23:1126-36 (2005).

International Preliminary Report on Patentability, PCT/EP2015/064409 (dated Dec. 27, 2016).

International Search Report and Written Opinion, PCT/EP2015/064409 (dated Sep. 14, 2015).

Jung et al., Design of interchain disulfide bonds in the framework region of the Fv fragment of the monoclonal antibody B3. *Proteins*, 19: 35-47 (1994).

Kabat et al., Sequences of Proteins of Immunological Interest, US Department of Health and Human Services (4th ed. 1983).

Kashmiri et al., SDR grafting—a new approach to antibody humanization. *Methods*. 36: 25-34 (2005).

Kettleborough et al., Isolation of tumor cell-specific single-chain Fv from immunized mice using phage-antibody libraries and the reconstruction of whole antibodies from these antibody fragments. *Eur. J. Immunol.* 24: 952-8 (1994).

(56) References Cited

OTHER PUBLICATIONS

Kohler et al., Continuous cultures of fused cells secreting antibody of predefined specificity. *Nature.* 256: 495-7 (1975).
Kontermann, Dual targeting strategies with bispecific antibodies, *MAbs.* 4:182-97 (2012).
Kozbor et al., The production of monoclonal antibodies from human lymphocytes. *Immunol. Today.* 4:72-9 (1983).
Lanaro et al., Red blood cell survival in patients with Hodgkin's disease. *Cancer.* 28: 658-61 (1971).
Low et al., Mimicking somatic hypermutation: affinity maturation of antibodies displayed on bacteriophage using a bacterial mutator strain, *J. Mol. Biol.* 260:359-68 (1996).
Lu et al., Fab-scFv fusion protein: an efficient approach to production of bispecific antibody fragments, *J. Immunol Methods.* 267:213-26 (2002).
Luo et al., Vl-linker-Vh orientation-dependent expression of single chain Fv-containing an engineered disulfide-stabilized bond in the framework regions. *J. Biochem.* 118: 825-31 (1995).
Luttgau et al., Immunotherapy of B-Cell lymphoma with an engineered bispecific antibody targeting CD19 and CD5, *Antibodies.* 2:338-52 (2013).
Madden et al., Applications of network BLAST server. *Meth. Enzymol.* 266: 131-41 (1996).
Marks et al., By-passing immunization: building high affinity human antibodies by chain shuffling. *Biotechnology.* 10: 779-83 (1992).
Mertens et al., New strategies in polypeptide and antibody synthesis: An overview. *Cancer Biother. Radiopharmaceut.* 19: 99-109 (2004).
Mertens, Empowered Antibodies Congress, Power Point Presentation, Jun. 17-18, 2015, Barcelona.
Metz et al., Bispecific antibody derivatives with restricted binding functionalities that are activated by proteolytic processing,*Protein Eng. Des. Sel.* 25:571-80 (2012).
Orcutt et al., A modular IgG-scFv bispecific antibody topology, *Protein Eng. Des. Sel.* 23:221-8 (2010).
Osol, Remington's Pharmaceutical Sciences, Mack Publishing Company, N.J. (16th ed. 1991).
Patten et al., Applications of DNA shuffling to pharmaceuticals and vaccines. *Curr. Opin. Biotechnol.* 8: 724-33 (1997).
Persic et al., An integrated vector system for the eukaryotic expression of antibodies or their fragments after selection from phage display libraries. *Gene.* 187: 9-18 (1997).
Rajagopal et al., A form of anti-Tac(Fv) which is both single-chain and disulfide stabilized: comparison with its single-chain and disulfide-stabilized homologs. *Protein Eng.* 10:1453-9 (1997).
Riechmann et al., Reshaping human antibodies for therapy, *Nature.* 332:323-4 (1998).
Reiter et al., Improved binding and antitumor activity of a recombinant anti-erbB2 immunotoxin by disulfide stabilization of the Fv fragment. *J. Biol. Chem.* 269: 18327-31 (1994).
Reiter et al., Stabilization of the Fv fragments in recombinant immunotoxins by disulfide bonds engineered into conserved framework regions. *Biochemistry.* 33: 5451-9 (1994).
Schanzer et al., Development of tetravalent, bispecific CCR5 antibodies with antiviral activity against CCR5 monoclonal antibody-resistant HIV-1 strains, *Antimicrob. Agents Chemother.* 55:2369-78 (2011).
Schoonjans et al., A new model for intermediate molecular weight recombinant bispecific and trispecific antibodies by efficient heterodimerization of single chain variable domains through fusion to a Fab-chain, *Biomol. Eng.* 17:193-202 (2001).
Schoonjans et al., Fab chains as an efficient heterodimerization scaffold for the production of recombinant bispecific and trispecific antibody derivatives. *J. Immunol.* 165: 7050-7 (2000).
Shen et al., Single variable domain antibody as a versatile building block for the construction of IgG-like bispecific antibodies, *J. Immunol. Methods.* 318:65-74 (2007).
Spiess et al., Alternative molecular formats and therapeutic applications for bispecific antibodies, *Mol. Immunol.* 67:95-106 (2015).

Thompson et al., Affinity maturation of a high-affinity human monoclonal antibody against the third hypervariable loop of human immunodeficiency virus: use of phage display to improve affinity and broaden strain reactivity. *J. Mol. Biol.* 256: 77-88 (1996).
Thorpe et al., The preparation and cytotoxic properties of antibody-toxin conjugates. *Immunol. Rev.* 62: 119-58 (1982).
Vaughan et al., Human antibodies by design. *Nat. Biotechnol.* 16: 535-9 (1998).
Verma et al., Antibody engineering: Comparision of bacterial yeast, insect and mammalian expression systems, *Journal of Immunological Methods.* 216:165-81 (1998).
Weatherill et al., Towards a universal disulphide stabilised single chain Fv format: importance of interchain disulphide bond location and vL-vH orientation, *Protein Eng. Des. Sel.* 25:321-9 (2012).
Wells et al., Cassette mutagenesis: an efficient method for generation of multiple mutations at defined sites. *Gene.* 34: 315-23 (1985).
Yang et al., CDR walking mutagenesis for the affinity maturation of a potent human anti-HIV-1 antibody into the picomolar range. *J. Mol. Biol.* 254: 392-403 (1995).
Young et al., Thermal stabilization of a single-chain Fv antibody fragment by introduction of a disulphide bond. *FEBS Lett.* 377:135-9 (1995).
Zhang et al., PowerBLAST: a new network BLAST application for interactive or automated sequence analysis and annotation. *Genome Res.* 7: 649-56 (1997).
Zhu et al., Remodeling domain interfaces to enhance heterodimer formation. *Protein Sci.* 6: 781-8 (1997).
Xiang et al., "Recent advances in antibody technique 2. Antibodies of small-molecule and composit function", Journal of Jinan University (Natoinal Science). 34:556-563 (2013).
Lu et al., "Acquired antagonistic activiity of bispecific diabody directed against two different epitopes on vascular endothelial growth factor receptor 2", Journal of Immunological Methods. 159-171 (1999).
Pan et al., "Blocking Neuropilin-1 Function Has an Additive Effect with Anti-VEGF to Inhibit Tumor Growth", Cancer Cell. 11:53-67 (2007).
Comoglio et al., "Drug development of MET inhibitors: targeting oncogene addiction and expedience", Nature Publishing Group. 7:504-516 (2008).
Di Zenzo et al., "The Intracellular and Extracellular Domains of BP180 Antigen Comprise Novel Epitopes Targeted by Pemphigoid Gestations Autoantibodies", Journal of Investigative Dermatology. 127: 864-873 (2006).
Luo et al., "V1-Linker-Vh Orientation-Dependent Expression of Single Chain Fv Containing an Enginerred Disulfide-Stabilized Bond in the Framework Regions", J. Biochem. 118, 825-831, (1995).
Roussel et al., "The structure of an entire noncovalent immunoglobulin kappa light-chain dimer (Bence-Jones protein) reveals a weak and unusual constant domains association", Eur. J. Biochem. 260, 192-199,(1999).
Qu et al., "Bispecific anti-CD20/22 antibodies inhibit B-cell lymphoma proliferation by a unique mechanism of action", Blood, 111:2211-2218, (2008).
Dong et al., "Stable IgG-like Bispecific Antibodies Directed toward the Type 1 Insulin-like Growth Factor Receptor Demonstrate Enhanced Ligand Blockade and Anti-tumor Activity", JBC, vol. 286:4703-4717, (2011).
Cao et al., "Characterization and analysis of scFv-IgG bispecific antibody size variants", mAbs 10:8, 1236-1247, (2018).
Swope et al., "Impact of enzymatic reduction on bivalent bispecific antibody fragmentation and loss of product purity upon reoxidation", Biotechnology and Bioengineering, 117:1063-1071, (2020).
Orcutt et al., "A modular IgG-scFv biospecific antibody topology", Protein Engineering, Design & Selection, 23:221-228, (2010).
Scahnzer et al., "Development of Tetravalent, Bispecific CCR5 Antibodies with Antiviral Activity against CCR5 Monoclonal Antibody-Resistant HIV-1 Strains", Antimicrobial Agents and Chemotherapy, 55:2369-2378, (2011).
Adams et al., "Extending the half-time of a fab fragment through generation of a humanized anti-human serum albumin Fv domain:

(56) References Cited

OTHER PUBLICATIONS

An investigation into the correlation between affinity and serum half-time", mAbs, 8:7, 1336-1346, (2016).
Rajagopal et al., "A form of anti-Tac(fv) which is both single-chain and disulfide stabilized: comparison with its single-chain and disulfide-stabilized homologs", Protein Engineering 10:1453-1459, (1997).
Reiter et. al., "Engineering antibody Fv fragments for cancer detection and therapy: Bisulfide-stabilized Fv fragments," Nature Biotechnology, vol. 14, 1239-1245, Oct. 1996
Sheikholvaezin et al. "Optimizing the generation of recombinant single-chain antibodies against placental alkaline phosphatase", Hybridoma, 25: 181-192, (2006).

\* cited by examiner

Figure 1:
Fab-2x dsscFv formats and Fab-dsscFv-dsFv format
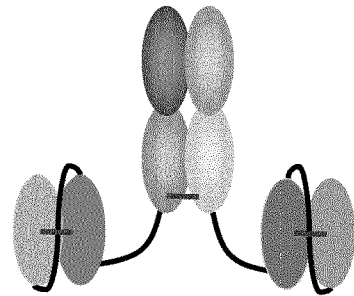
Fab#2-(HC)-dsscFv#3-(LC)-dsscFv#4
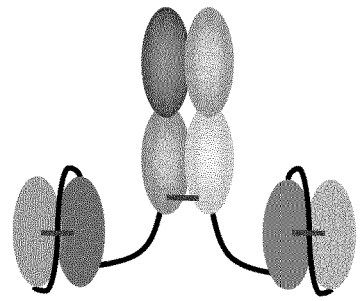
Fab#2-(LC)-dsscFv#3-(HC)-dsscFv#4
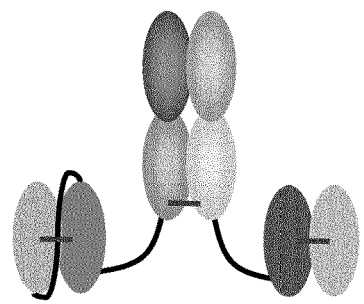
Fab-(HC)dsscFv-(LC)dsFv
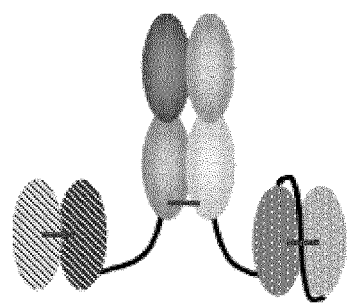
Fab-(HC)dsFv-(LC)dsscFv SDS-PAGE analysis of protein G-purified, HEK293-expressed Fab-1xdsscFv, 1xscFv and Fab-2xdsscFv proteins 1. Fab#2-(HC) dsHLscFv#3, (LC) HLscFv#4
2. Fab#2-(HC)dsHLscFv#3, (LC)dsHLscFv#4
3. Fab#2-(HC)dsHLscFv#3, (LC)LHscFv#4
4. Fab#2-(HC)dsHLscFv#3, (LC)dsLHscFv#4

5. Fab#2-(LC)dsHLscFv#3, (HC)HLscFv#4
6. Fab#2-(LC)dsHLscFv#3, (HC)dsHLscFv#4
7. Fab#2-(LC)dsHLscFv#3, (HC)LHscFv#4
8. Fab#2-(LC)dsHLscFv#3, (HC)dsLHscFv#4

Figure 3: G3000 SE HPLC analysis of protein G-purified, HEK293-expressed Fab-1xdsscFv, 1xscFv and Fab-2xdsscFv proteins
1. Fab#2 HC-dsHL#3 LC-HL#4: 86% monomer 2. Fab#2 HC-dsHL#3 LC-dsHL#4: 89% monomer
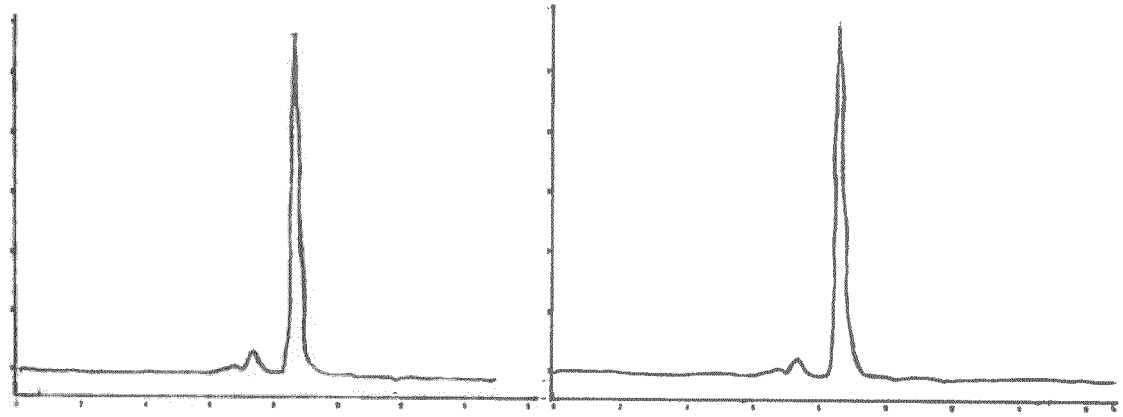
3. Fab#2 HC-dsHL#3 LC-LH: 84% monomer 4. Fab#2 HC-dsHL#3 LC-dsLH#4: 83% monomer
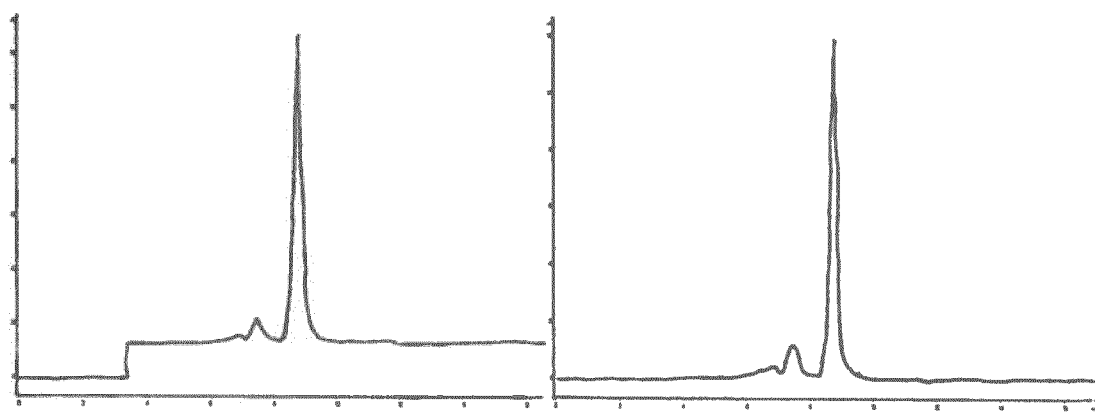
5. Fab#2 LC-dsHL#3 HC-HL#4: 85% monomer 6. Fab#2 LC-dsHL#3 HC-dsHL#4: 88% monomer
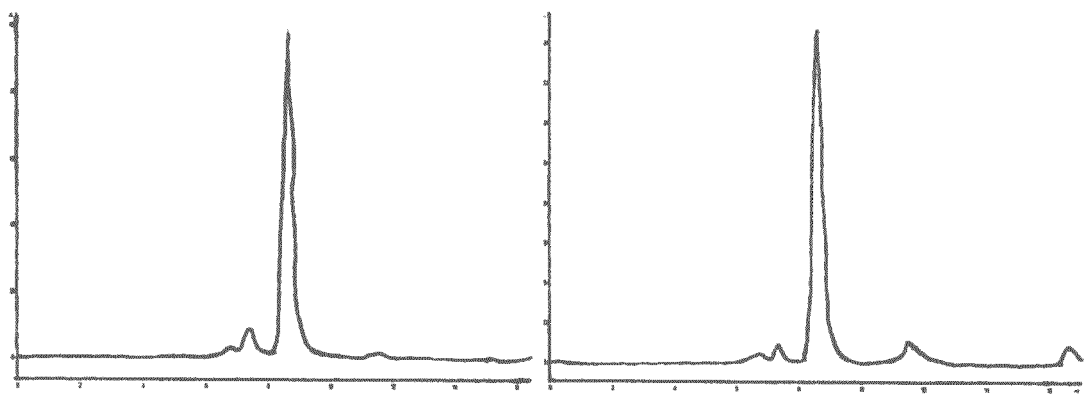

Figure 3 continued
7. Fab#2 LC-dsHL#3 HC-LH#4: 88% monomer  8. Fab#2 LC-dsHL#3 HC-dsLH#4: 83% monomer
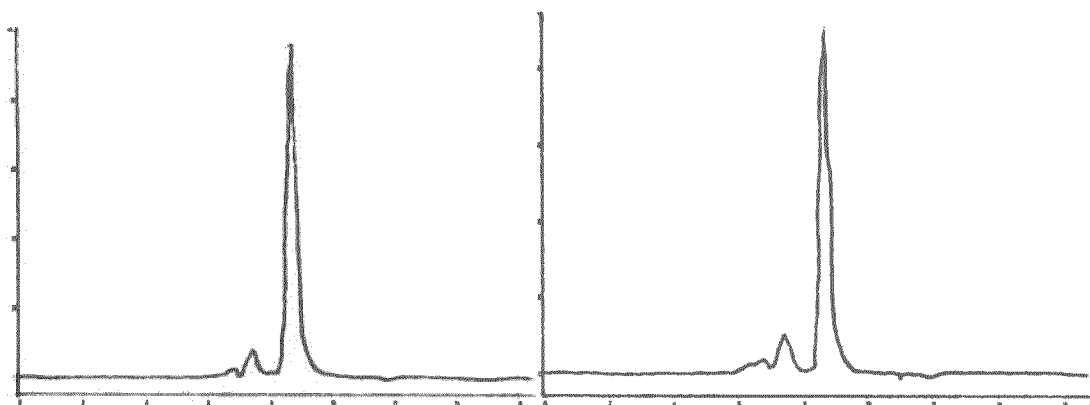
Figure 4: SDS-PAGE analysis of purified, HEK293-expressed Fab-2xdsscFv#3 proteins
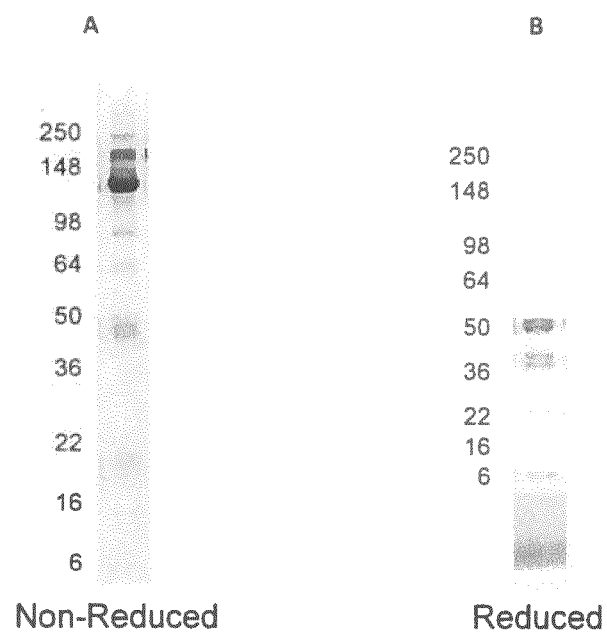
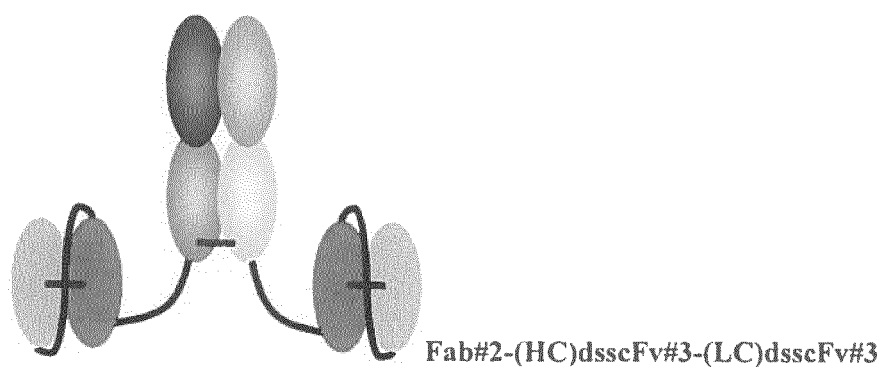
Fab#2-(HC)dsscFv#3-(LC)dsscFv#3

Figure 5: S200 SE HPLC analysis of purified, HEK293-expressed Fab-2xdsscFv#3 proteins
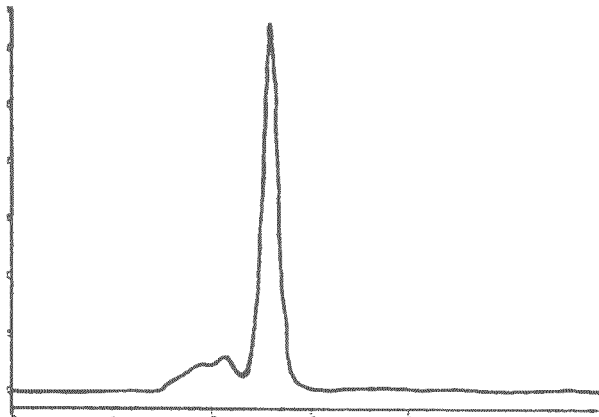
Figure 6: SDS-PAGE analysis of protein G-purified, HEK293 expressed Fab#2-(HC)dsscFv#3-(LC) dsscFv#1 and Fab#2-(HC)dsscFv#3-(LC)dsFv#1 (LC-vL linked) proteins
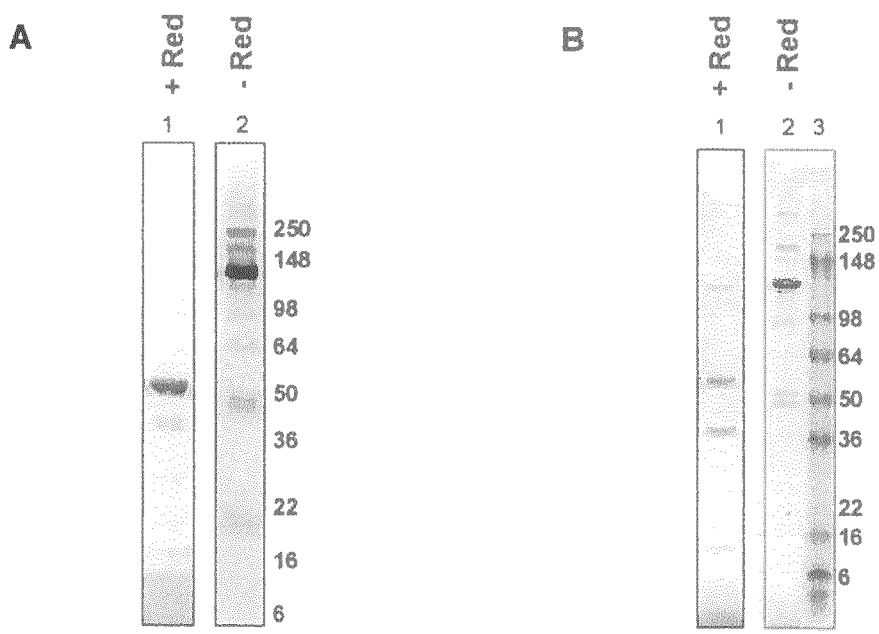
A
1. Fab#2-(HC)dsscFv#3-(LC)dsscFv#1, reduced
2. Fab#2-(HC)dsscFv#3-(LC)dsscFv#1, non-reduced
B
1. Fab#2-(HC)dsscFv#3-(LC)dsFv#1, reduced
2. Fab#2-(HC)dsscFv#3-(LC)dsFv#1, non-reduced
3. SeeBluePlus2 MW ladder Figure 6 Continued
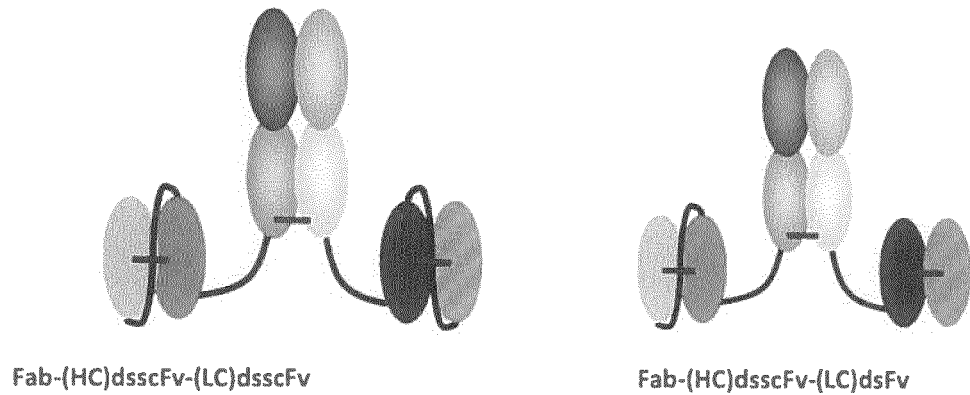
Fab-(HC)dsscFv-(LC)dsscFv        Fab-(HC)dsscFv-(LC)dsFv
Figure 7: G3000 SE HPLC analysis of protein G-purified, HEK293 expressed Fab#2-(HC)dsscFv#3-(LC)dsscFv#1 and Fab#2-(HC)dsscFv#3-(LC)dsFv#1 (LC-vL linked) proteins
Fab#2-(HC)dsscFv#3-(LC)dsFv#1: 91% monomer
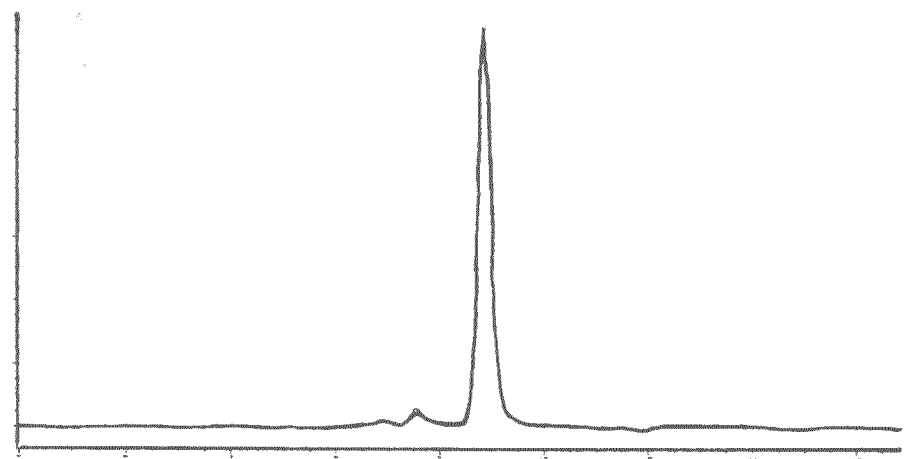
Fab#2-(HC)dsscFv#3-(LC)dsscFv#1: 30% monomer
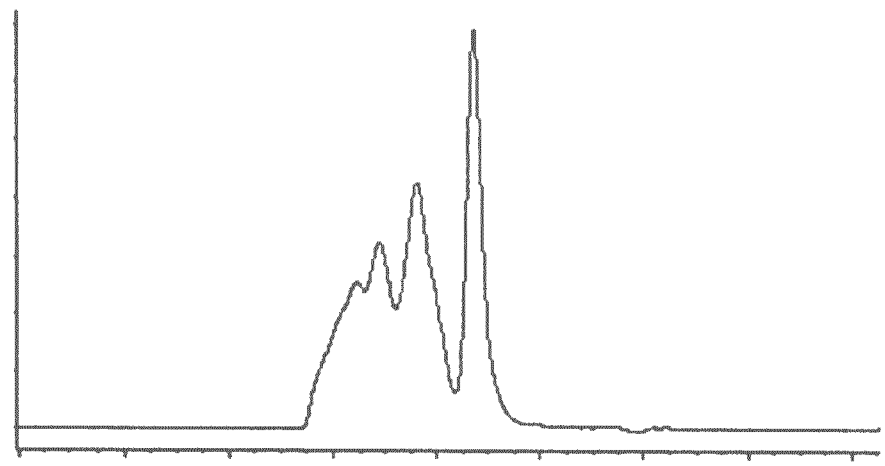

Figure 8     SDS-PAGE Analysis under Reducing Conditions
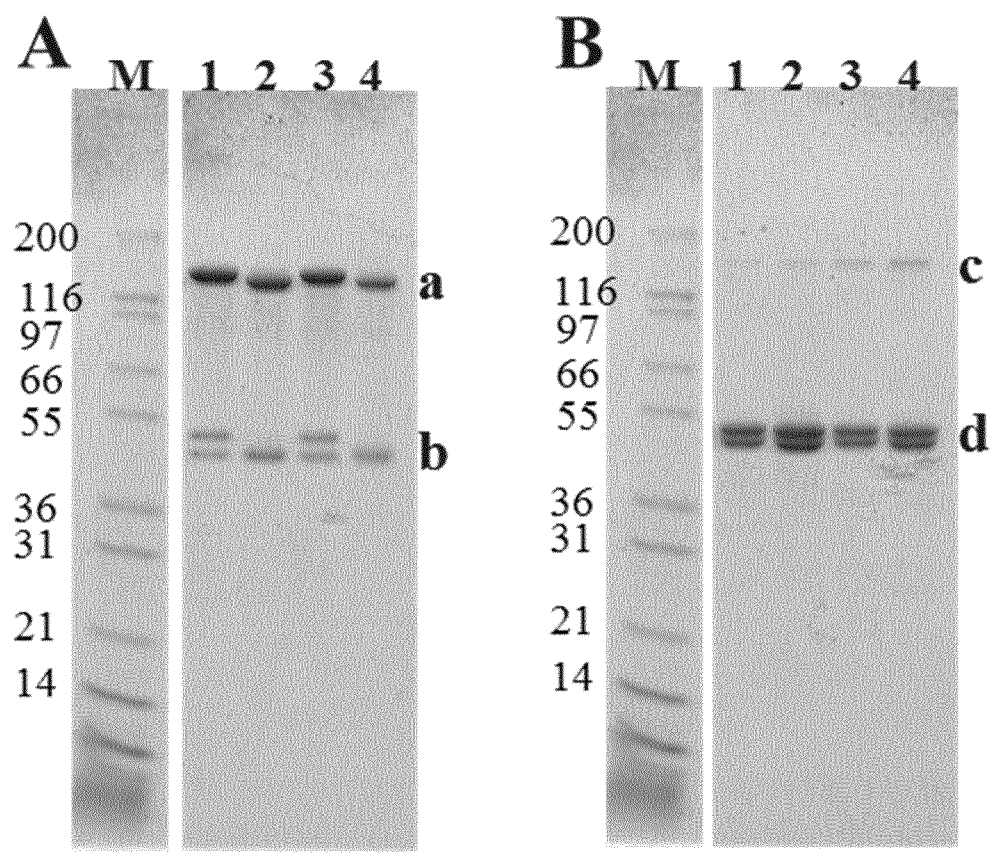
M: Mark12 protein standard (Life Technologies)
1. Fab#2-(LC)dsHLscFv#3,(HC)HLscFv#4
2. Fab#2-(LC)dsHLscFv#3,(HC)dsHLscFv#4
3. Fab#2-(LC)dsHLscFv#3,(HC)LHscFv#4
4. Fab#2-(LC)dsHLscFv#3,(HC)dsLHscFv#4

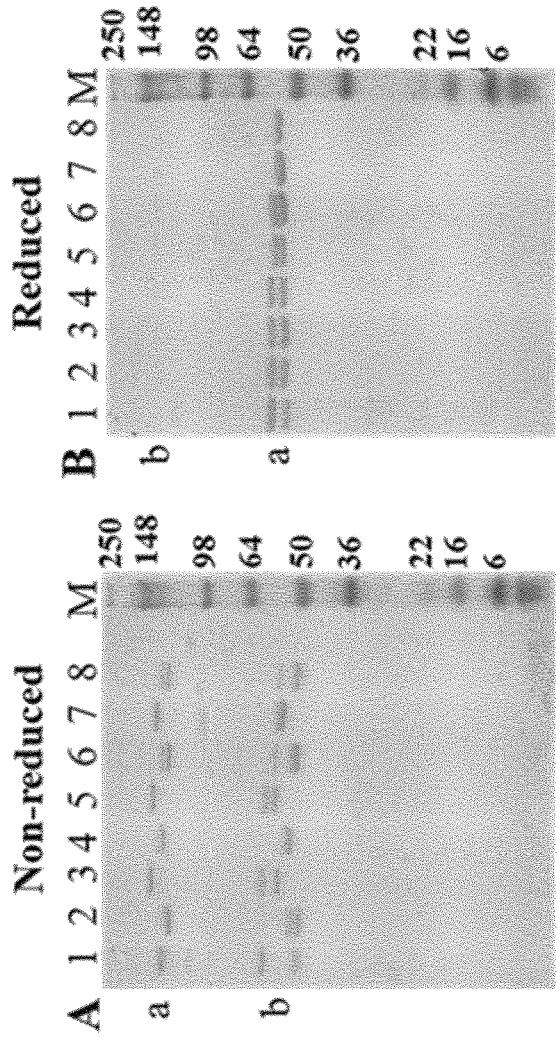
Figure 10 SDS-PAGE analysis of Protein-G purified, EXPiHEK expressed Fab-2xscFv and Fab-2xdsscFv formats
1. Fab#4-(LC)HLscFv#5,(HC)HLscFv#6
2. Fab#4-(LC)dsHLscFv#5,(HC)dsHLscFv#6
3. Fab#4-(LC)HLscFv#7,(HC)HLscFv#8
4. Fab#4-(LC)dsHLscFv#7,(HC)dsHLscFv#8
5. Fab#4-(LC) HLscFv#9,(HC)LHscFv#10
6. Fab#4-(LC)dsHLscFv#9,(HC)dsLHscFv#10
7. Fab#4-(LC)HLscFv#7,(HC)LHscFv#10
8. Fab#4-(LC)dsHLscFv#7,(HC)dsLHscFv#10
M. Seeblue2 protein standard markers (Life Technologies)

SEQUENCE LISTING

<160> NUMBER OF SEQ ID NOS: 80

<210> SEQ ID NO 1
<211> LENGTH: 11
<212> TYPE: PRT
<213> ORGANISM: Artificial Sequence
<220> FEATURE:
<223> OTHER INFORMATION: Peptide Linker

<400> SEQUENCE: 1

Ser Gly Gly Gly Gly Thr Gly Gly Gly Ser
1               5                   10

<210> SEQ ID NO 2
<211> LENGTH: 11
<212> TYPE: PRT
<213> ORGANISM: Artificial Sequence
<220> FEATURE:
<223> OTHER INFORMATION: Peptide Linker

<400> SEQUENCE: 2

Ser Gly Gly Gly Gly Ser Gly Gly Gly Gly Ser
1               5                   10

<210> SEQ ID NO 3
<211> LENGTH: 8
<212> TYPE: PRT
<213> ORGANISM: Artificial Sequence
<220> FEATURE:
<223> OTHER INFORMATION: Hinge linker

<400> SEQUENCE: 3

Asp Lys Thr His Thr Cys Ala Ala
1               5

<210> SEQ ID NO 4
<211> LENGTH: 11
<212> TYPE: PRT
<213> ORGANISM: Artificial Sequence
<220> FEATURE:
<223> OTHER INFORMATION: Hinge linker

<400> SEQUENCE: 4

Asp Lys Thr His Thr Cys Pro Pro Cys Pro Ala
1               5                   10

<210> SEQ ID NO 5
<211> LENGTH: 18
<212> TYPE: PRT
<213> ORGANISM: Artificial Sequence
<220> FEATURE:
<223> OTHER INFORMATION: Hinge linker

<400> SEQUENCE: 5

Asp Lys Thr His Thr Cys Pro Pro Cys Pro Ala Thr Cys Pro Pro Cys
1               5                   10                  15

Pro Ala

<210> SEQ ID NO 6
<211> LENGTH: 25
<212> TYPE: PRT
<213> ORGANISM: Artificial Sequence
<220> FEATURE:
<223> OTHER INFORMATION: Hinge linker

<400> SEQUENCE: 6

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 7
<211> LENGTH: 30

<212> TYPE: PRT
<213> ORGANISM: Artificial Sequence
<220> FEATURE:
<223> OTHER INFORMATION: Hinge linker

<400> SEQUENCE: 7

Asp Lys Thr His Thr Cys Pro Pro Cys Pro Ala Gly Lys Pro Thr Leu
1               5                   10                  15
Tyr Asn Ser Leu Val Met Ser Asp Thr Ala Gly Thr Cys Tyr
            20                  25                  30

<210> SEQ ID NO 8
<211> LENGTH: 31
<212> TYPE: PRT
<213> ORGANISM: Artificial Sequence
<220> FEATURE:
<223> OTHER INFORMATION: Hinge linker

<400> SEQUENCE: 8

Asp Lys Thr His Thr Cys Pro Pro Cys Pro Ala Gly Lys Pro Thr His
1               5                   10                  15
Val Asn Val Ser Val Val Met Ala Glu Val Asp Gly Thr Cys Tyr
            20                  25                  30

<210> SEQ ID NO 9
<211> LENGTH: 15
<212> TYPE: PRT
<213> ORGANISM: Artificial Sequence
<220> FEATURE:
<223> OTHER INFORMATION: Hinge linker

<400> SEQUENCE: 9

Asp Lys Thr His Thr Cys Cys Val Glu Cys Pro Pro Cys Pro Ala
1               5                   10                  15

<210> SEQ ID NO 10
<211> LENGTH: 26
<212> TYPE: PRT
<213> ORGANISM: Artificial Sequence
<220> FEATURE:
<223> OTHER INFORMATION: Hinge linker

<400> SEQUENCE: 10

Asp Lys Thr His Thr Cys Pro Arg Cys Pro Glu Pro Lys Ser Cys Asp
1               5                   10                  15
Thr Pro Pro Pro Cys Pro Arg Cys Pro Ala
            20                  25

<210> SEQ ID NO 11
<211> LENGTH: 11
<212> TYPE: PRT
<213> ORGANISM: Artificial Sequence
<220> FEATURE:
<223> OTHER INFORMATION: Hinge linker

<400> SEQUENCE: 11

Asp Lys Thr His Thr Cys Pro Ser Cys Pro Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: Flexible linker

```
<400> SEQUENCE: 12

Ser Gly Gly Gly Gly Ser Glu
1               5

<210> SEQ ID NO 13
<211> LENGTH: 6
<212> TYPE: PRT
<213> ORGANISM: Artificial Sequence
<220> FEATURE:
<223> OTHER INFORMATION: Flexible linker

<400> SEQUENCE: 13

Asp Lys Thr His Thr Ser
1               5

<210> SEQ ID NO 14
<211> LENGTH: 6
<212> TYPE: PRT
<213> ORGANISM: Artificial Sequence
<220> FEATURE:
<223> OTHER INFORMATION: Flexible linker

<400> SEQUENCE: 14

Ser Gly Gly Gly Gly Ser
1               5

<210> SEQ ID NO 15
<211> LENGTH: 11
<212> TYPE: PRT
<213> ORGANISM: Artificial Sequence
<220> FEATURE:
<223> OTHER INFORMATION: Flexible linker

<400> SEQUENCE: 15

Ser Gly Gly Gly Gly Ser Gly Gly Gly Gly Ser
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Flexible linker

<400> SEQUENCE: 16

Ser Gly Gly Gly Gly Ser Gly Gly Gly Ser Gly Gly Gly Gly Ser
1               5                   10                  15

<210> SEQ ID NO 17
<211> LENGTH: 21
<212> TYPE: PRT
<213> ORGANISM: Artificial Sequence
<220> FEATURE:
<223> OTHER INFORMATION: Flexible linker

<400> SEQUENCE: 17

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 18
<211> LENGTH: 26
<212> TYPE: PRT
<213> ORGANISM: Artificial Sequence
<220> FEATURE:
```

```
<223> OTHER INFORMATION: Flexible linker

<400> SEQUENCE: 18

Ser Gly Gly Gly Gly Ser Gly Gly Gly Ser Gly Gly Gly Gly Ser
1               5                   10                  15

Gly Gly Gly Gly Ser Gly Gly Gly Gly Ser
            20                  25

<210> SEQ ID NO 19
<211> LENGTH: 11
<212> TYPE: PRT
<213> ORGANISM: Artificial Sequence
<220> FEATURE:
<223> OTHER INFORMATION: Flexible linker

<400> SEQUENCE: 19

Ala Ala Ala Gly Ser Gly Gly Ala Ser Ala Ser
1               5                   10

<210> SEQ ID NO 20
<211> LENGTH: 16
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid

<400> SEQUENCE: 20

Ala Ala Ala Gly Ser Gly Xaa Gly Gly Gly Ser Gly Ala Ser Ala Ser
1               5                   10                  15

<210> SEQ ID NO 21
<211> LENGTH: 21
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid

<400> SEQUENCE: 21

Ala Ala Ala Gly Ser Gly Xaa Gly Gly Gly Ser Xaa Gly Gly Gly Ser
1               5                   10                  15

Gly Ala Ser Ala Ser
            20

<210> SEQ ID NO 22
<211> LENGTH: 26
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid
```

```
<220> FEATURE:
<221> NAME/KEY: misc_feature
<222> LOCATION: (17)..(17)
<223> OTHER INFORMATION: Xaa can be naturally occuring amino acid

<400> SEQUENCE: 22

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 23
<211> LENGTH: 31
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid
<220> FEATURE:
<221> NAME/KEY: misc_feature
<222> LOCATION: (12)..(12)
<223> OTHER INFORMATION: Xaa can be naturally occuring amino acid
<220> FEATURE:
<221> NAME/KEY: misc_feature
<222> LOCATION: (17)..(17)
<223> OTHER INFORMATION: Xaa can be naturally occuring amino acid
<220> FEATURE:
<221> NAME/KEY: misc_feature
<222> LOCATION: (22)..(22)
<223> OTHER INFORMATION: Xaa can be naturally occuring amino acid

<400> SEQUENCE: 23

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 24
<211> LENGTH: 13
<212> TYPE: PRT
<213> ORGANISM: Artificial Sequence
<220> FEATURE:
<223> OTHER INFORMATION: Flexible linker
<220> FEATURE:
<221> NAME/KEY: misc_feature
<222> LOCATION: (7)..(7)
<223> OTHER INFORMATION: Xaa can be naturally occuring amino acid

<400> SEQUENCE: 24

Ala Ala Ala Gly Ser Gly Xaa Ser Gly Ala Ser Ala Ser
1               5                   10

<210> SEQ ID NO 25
<211> LENGTH: 28
<212> TYPE: PRT
<213> ORGANISM: Artificial Sequence
<220> FEATURE:
<223> OTHER INFORMATION: Flexible linker

<400> SEQUENCE: 25

Pro Gly Gly Asn Arg Gly Thr Thr Thr Thr Arg Arg Pro Ala Thr Thr
1               5                   10                  15

Thr Gly Ser Ser Pro Gly Pro Thr Gln Ser His Tyr
            20                  25
```

```
<210> SEQ ID NO 26
<211> LENGTH: 11
<212> TYPE: PRT
<213> ORGANISM: Artificial Sequence
<220> FEATURE:
<223> OTHER INFORMATION: Flexible linker

<400> SEQUENCE: 26

Ala Thr Thr Thr Gly Ser Ser Pro Gly Pro Thr
1               5                   10

<210> SEQ ID NO 27
<211> LENGTH: 6
<212> TYPE: PRT
<213> ORGANISM: Artificial Sequence
<220> FEATURE:
<223> OTHER INFORMATION: Flexible linker

<400> SEQUENCE: 27

Ala Thr Thr Thr Gly Ser
1               5

<210> SEQ ID NO 28
<211> LENGTH: 21
<212> TYPE: PRT
<213> ORGANISM: Artificial Sequence
<220> FEATURE:
<223> OTHER INFORMATION: Flexible linker

<400> SEQUENCE: 28

Glu Pro Ser Gly Pro Ile Ser Thr Ile Asn Ser Pro Pro Ser Lys Glu
1               5                   10                  15

Ser His Lys Ser Pro
            20

<210> SEQ ID NO 29
<211> LENGTH: 15
<212> TYPE: PRT
<213> ORGANISM: Artificial Sequence
<220> FEATURE:
<223> OTHER INFORMATION: Flexible linker

<400> SEQUENCE: 29

Gly Thr Val Ala Ala Pro Ser Val Phe Ile Phe Pro Pro Ser Asp
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Flexible linker

<400> SEQUENCE: 30

Gly Gly Gly Gly Ile Ala Pro Ser Met Val Gly Gly Gly Gly Ser
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Flexible linker

<400> SEQUENCE: 31

Gly Gly Gly Gly Lys Val Glu Gly Ala Gly Gly Gly Gly Gly Ser
1               5                   10                  15
```

<210> SEQ ID NO 32
<211> LENGTH: 15
<212> TYPE: PRT
<213> ORGANISM: Artificial Sequence
<220> FEATURE:
<223> OTHER INFORMATION: Flexible linker

<400> SEQUENCE: 32

Gly Gly Gly Gly Ser Met Lys Ser His Asp Gly Gly Gly Gly Ser
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: Flexible linker

<400> SEQUENCE: 33

Gly Gly Gly Gly Asn Leu Ile Thr Ile Val Gly Gly Gly Gly Ser
1               5                   10                  15

<210> SEQ ID NO 34
<211> LENGTH: 15
<212> TYPE: PRT
<213> ORGANISM: Artificial Sequence
<220> FEATURE:
<223> OTHER INFORMATION: Flexible linker

<400> SEQUENCE: 34

Gly Gly Gly Gly Val Val Pro Ser Leu Pro Gly Gly Gly Gly Ser
1               5                   10                  15

<210> SEQ ID NO 35
<211> LENGTH: 12
<212> TYPE: PRT
<213> ORGANISM: Artificial Sequence
<220> FEATURE:
<223> OTHER INFORMATION: Flexible linker

<400> SEQUENCE: 35

Gly Gly Glu Lys Ser Ile Pro Gly Gly Gly Gly Ser
1               5                   10

<210> SEQ ID NO 36
<211> LENGTH: 18
<212> TYPE: PRT
<213> ORGANISM: Artificial Sequence
<220> FEATURE:
<223> OTHER INFORMATION: Flexible linker

<400> SEQUENCE: 36

Arg Pro Leu Ser Tyr Arg Pro Pro Phe Pro Phe Gly Phe Pro Ser Val
1               5                   10                  15

Arg Pro

<210> SEQ ID NO 37
<211> LENGTH: 18
<212> TYPE: PRT
<213> ORGANISM: Artificial Sequence
<220> FEATURE:
<223> OTHER INFORMATION: Flexible linker

<400> SEQUENCE: 37

Tyr Pro Arg Ser Ile Tyr Ile Arg Arg Arg His Pro Ser Pro Ser Leu

```
1               5                   10                  15

Thr Thr

<210> SEQ ID NO 38
<211> LENGTH: 18
<212> TYPE: PRT
<213> ORGANISM: Artificial Sequence
<220> FEATURE:
<223> OTHER INFORMATION: Flexible linker

<400> SEQUENCE: 38

Thr Pro Ser His Leu Ser His Ile Leu Pro Ser Phe Gly Leu Pro Thr
1               5                   10                  15

Phe Asn

<210> SEQ ID NO 39
<211> LENGTH: 18
<212> TYPE: PRT
<213> ORGANISM: Artificial Sequence
<220> FEATURE:
<223> OTHER INFORMATION: Flexible linker

<400> SEQUENCE: 39

Arg Pro Val Ser Pro Phe Thr Phe Pro Arg Leu Ser Asn Ser Trp Leu
1               5                   10                  15

Pro Ala

<210> SEQ ID NO 40
<211> LENGTH: 18
<212> TYPE: PRT
<213> ORGANISM: Artificial Sequence
<220> FEATURE:
<223> OTHER INFORMATION: Flexible linker

<400> SEQUENCE: 40

Ser Pro Ala Ala His Phe Pro Arg Ser Ile Pro Arg Pro Gly Pro Ile
1               5                   10                  15

Arg Thr

<210> SEQ ID NO 41
<211> LENGTH: 18
<212> TYPE: PRT
<213> ORGANISM: Artificial Sequence
<220> FEATURE:
<223> OTHER INFORMATION: Flexible linker

<400> SEQUENCE: 41

Ala Pro Gly Pro Ser Ala Pro Ser His Arg Ser Leu Pro Ser Arg Ala
1               5                   10                  15

Phe Gly

<210> SEQ ID NO 42
<211> LENGTH: 18
<212> TYPE: PRT
<213> ORGANISM: Artificial Sequence
<220> FEATURE:
<223> OTHER INFORMATION: Flexible linker

<400> SEQUENCE: 42

Pro Arg Asn Ser Ile His Phe Leu His Pro Leu Leu Val Ala Pro Leu
1               5                   10                  15

Gly Ala
```

```
<210> SEQ ID NO 43
<211> LENGTH: 18
<212> TYPE: PRT
<213> ORGANISM: Artificial Sequence
<220> FEATURE:
<223> OTHER INFORMATION: Flexible linker

<400> SEQUENCE: 43

Met Pro Ser Leu Ser Gly Val Leu Gln Val Arg Tyr Leu Ser Pro Pro
1               5                   10                  15

Asp Leu

<210> SEQ ID NO 44
<211> LENGTH: 18
<212> TYPE: PRT
<213> ORGANISM: Artificial Sequence
<220> FEATURE:
<223> OTHER INFORMATION: Flexible linker

<400> SEQUENCE: 44

Ser Pro Gln Tyr Pro Ser Pro Leu Thr Leu Thr Leu Pro Pro His Pro
1               5                   10                  15

Ser Leu

<210> SEQ ID NO 45
<211> LENGTH: 18
<212> TYPE: PRT
<213> ORGANISM: Artificial Sequence
<220> FEATURE:
<223> OTHER INFORMATION: Flexible linker

<400> SEQUENCE: 45

Asn Pro Ser Leu Asn Pro Pro Ser Tyr Leu His Arg Ala Pro Ser Arg
1               5                   10                  15

Ile Ser

<210> SEQ ID NO 46
<211> LENGTH: 17
<212> TYPE: PRT
<213> ORGANISM: Artificial Sequence
<220> FEATURE:
<223> OTHER INFORMATION: Flexible linker

<400> SEQUENCE: 46

Leu Pro Trp Arg Thr Ser Leu Leu Pro Ser Leu Pro Leu Arg Arg Arg
1               5                   10                  15

Pro

<210> SEQ ID NO 47
<211> LENGTH: 18
<212> TYPE: PRT
<213> ORGANISM: Artificial Sequence
<220> FEATURE:
<223> OTHER INFORMATION: Flexible linker

<400> SEQUENCE: 47

Pro Pro Leu Phe Ala Lys Gly Pro Val Gly Leu Leu Ser Arg Ser Phe
1               5                   10                  15

Pro Pro

<210> SEQ ID NO 48
<211> LENGTH: 18
<212> TYPE: PRT
```

```
<213> ORGANISM: Artificial Sequence
<220> FEATURE:
<223> OTHER INFORMATION: Flexible linker

<400> SEQUENCE: 48

Val Pro Pro Ala Pro Val Val Ser Leu Arg Ser Ala His Ala Arg Pro
1               5                   10                  15

Pro Tyr

<210> SEQ ID NO 49
<211> LENGTH: 17
<212> TYPE: PRT
<213> ORGANISM: Artificial Sequence
<220> FEATURE:
<223> OTHER INFORMATION: Flexible linker

<400> SEQUENCE: 49

Leu Arg Pro Thr Pro Pro Arg Val Arg Ser Tyr Thr Cys Cys Pro Thr
1               5                   10                  15

Pro

<210> SEQ ID NO 50
<211> LENGTH: 18
<212> TYPE: PRT
<213> ORGANISM: Artificial Sequence
<220> FEATURE:
<223> OTHER INFORMATION: Flexible linker

<400> SEQUENCE: 50

Pro Asn Val Ala His Val Leu Pro Leu Leu Thr Val Pro Trp Asp Asn
1               5                   10                  15

Leu Arg

<210> SEQ ID NO 51
<211> LENGTH: 18
<212> TYPE: PRT
<213> ORGANISM: Artificial Sequence
<220> FEATURE:
<223> OTHER INFORMATION: Flexible linker

<400> SEQUENCE: 51

Cys Asn Pro Leu Leu Pro Leu Cys Ala Arg Ser Pro Ala Val Arg Thr
1               5                   10                  15

Phe Pro

<210> SEQ ID NO 52
<211> LENGTH: 11
<212> TYPE: PRT
<213> ORGANISM: Artificial Sequence
<220> FEATURE:
<223> OTHER INFORMATION: rigid linker

<400> SEQUENCE: 52

Gly Ala Pro Ala Pro Ala Ala Pro Ala Pro Ala
1               5                   10

<210> SEQ ID NO 53
<211> LENGTH: 4
<212> TYPE: PRT
<213> ORGANISM: Artificial Sequence
<220> FEATURE:
<223> OTHER INFORMATION: rigid linker

<400> SEQUENCE: 53
```

```
Pro Pro Pro Pro
1
```

```
<210> SEQ ID NO 54
<211> LENGTH: 11
<212> TYPE: PRT
<213> ORGANISM: Artificial Sequence
<220> FEATURE:
<223> OTHER INFORMATION: albumin binding peptide

<400> SEQUENCE: 54

Asp Leu Cys Leu Arg Asp Trp Gly Cys Leu Trp
1               5                   10
```

```
<210> SEQ ID NO 55
<211> LENGTH: 11
<212> TYPE: PRT
<213> ORGANISM: Artificial Sequence
<220> FEATURE:
<223> OTHER INFORMATION: albumin binding peptide

<400> SEQUENCE: 55

Asp Ile Cys Leu Pro Arg Trp Gly Cys Leu Trp
1               5                   10
```

```
<210> SEQ ID NO 56
<211> LENGTH: 15
<212> TYPE: PRT
<213> ORGANISM: Artificial Sequence
<220> FEATURE:
<223> OTHER INFORMATION: albumin binding peptide

<400> SEQUENCE: 56

Met Glu Asp Ile Cys Leu Pro Arg Trp Gly Cys Leu Trp Gly Asp
1               5                   10                  15
```

```
<210> SEQ ID NO 57
<211> LENGTH: 20
<212> TYPE: PRT
<213> ORGANISM: Artificial Sequence
<220> FEATURE:
<223> OTHER INFORMATION: albumin binding peptide

<400> SEQUENCE: 57

Gln Arg Leu Met Glu Asp Ile Cys Leu Pro Arg Trp Gly Cys Leu Trp
1               5                   10                  15

Glu Asp Asp Glu
            20
```

```
<210> SEQ ID NO 58
<211> LENGTH: 20
<212> TYPE: PRT
<213> ORGANISM: Artificial Sequence
<220> FEATURE:
<223> OTHER INFORMATION: albumin binding peptide

<400> SEQUENCE: 58

Gln Gly Leu Ile Gly Asp Ile Cys Leu Pro Arg Trp Gly Cys Leu Trp
1               5                   10                  15

Gly Arg Ser Val
            20
```

```
<210> SEQ ID NO 59
<211> LENGTH: 21
<212> TYPE: PRT
<213> ORGANISM: Artificial Sequence
```

```
<220> FEATURE:
<223> OTHER INFORMATION: albumin binding peptide

<400> SEQUENCE: 59

Gln Gly Leu Ile Gly Asp Ile Cys Leu Pro Arg Trp Gly Cys Leu Trp
1               5                   10                  15

Gly Arg Ser Val Lys
            20

<210> SEQ ID NO 60
<211> LENGTH: 15
<212> TYPE: PRT
<213> ORGANISM: Artificial Sequence
<220> FEATURE:
<223> OTHER INFORMATION: albumin binding peptide

<400> SEQUENCE: 60

Glu Asp Ile Cys Leu Pro Arg Trp Gly Cys Leu Trp Glu Asp Asp
1               5                   10                  15

<210> SEQ ID NO 61
<211> LENGTH: 18
<212> TYPE: PRT
<213> ORGANISM: Artificial Sequence
<220> FEATURE:
<223> OTHER INFORMATION: albumin binding peptide

<400> SEQUENCE: 61

Arg Leu Met Glu Asp Ile Cys Leu Pro Arg Trp Gly Cys Leu Trp Glu
1               5                   10                  15

Asp Asp

<210> SEQ ID NO 62
<211> LENGTH: 16
<212> TYPE: PRT
<213> ORGANISM: Artificial Sequence
<220> FEATURE:
<223> OTHER INFORMATION: albumin binding peptide

<400> SEQUENCE: 62

Met Glu Asp Ile Cys Leu Pro Arg Trp Gly Cys Leu Trp Glu Asp Asp
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: albumin binding peptide

<400> SEQUENCE: 63

Met Glu Asp Ile Cys Leu Pro Arg Trp Gly Cys Leu Trp Glu Asp
1               5                   10                  15

<210> SEQ ID NO 64
<211> LENGTH: 18
<212> TYPE: PRT
<213> ORGANISM: Artificial Sequence
<220> FEATURE:
<223> OTHER INFORMATION: albumin binding peptide

<400> SEQUENCE: 64

Arg Leu Met Glu Asp Ile Cys Leu Ala Arg Trp Gly Cys Leu Trp Glu
1               5                   10                  15

Asp Asp
```

<210> SEQ ID NO 65
<211> LENGTH: 20
<212> TYPE: PRT
<213> ORGANISM: Artificial Sequence
<220> FEATURE:
<223> OTHER INFORMATION: albumin binding peptide

<400> SEQUENCE: 65

Glu Val Arg Ser Phe Cys Thr Arg Trp Pro Ala Glu Lys Ser Cys Lys
1               5                   10                  15

Pro Leu Arg Gly
            20

<210> SEQ ID NO 66
<211> LENGTH: 20
<212> TYPE: PRT
<213> ORGANISM: Artificial Sequence
<220> FEATURE:
<223> OTHER INFORMATION: albumin binding peptide

<400> SEQUENCE: 66

Arg Ala Pro Glu Ser Phe Val Cys Tyr Trp Glu Thr Ile Cys Phe Glu
1               5                   10                  15

Arg Ser Glu Gln
            20

<210> SEQ ID NO 67
<211> LENGTH: 11
<212> TYPE: PRT
<213> ORGANISM: Artificial Sequence
<220> FEATURE:
<223> OTHER INFORMATION: albumin binding peptide

<400> SEQUENCE: 67

Glu Met Cys Tyr Phe Pro Gly Ile Cys Trp Met
1               5                   10

<210> SEQ ID NO 68
<211> LENGTH: 20
<212> TYPE: PRT
<213> ORGANISM: Artificial Sequence
<220> FEATURE:
<223> OTHER INFORMATION: albumin binding peptide

<400> SEQUENCE: 68

Gly Gly Gly Gly Ser Gly Gly Gly Ser Gly Gly Gly Gly Ser Gly
1               5                   10                  15

Gly Gly Gly Ser
            20

<210> SEQ ID NO 69
<211> LENGTH: 16
<212> TYPE: PRT
<213> ORGANISM: Artificial Sequence
<220> FEATURE:
<223> OTHER INFORMATION: flexible linker

<400> SEQUENCE: 69

Ser Gly Gly Gly Gly Ser Gly Gly Gly Gly Ser Gly Gly Gly Gly Ser
1               5                   10                  15

<210> SEQ ID NO 70
<211> LENGTH: 16
<212> TYPE: PRT

```
<213> ORGANISM: Artificial Sequence
<220> FEATURE:
<223> OTHER INFORMATION: flexible linker

<400> SEQUENCE: 70

Ser Gly Gly Gly Gly Ser Gly Gly Gly Thr Gly Gly Gly Ser
1               5                   10                  15

<210> SEQ ID NO 71
<211> LENGTH: 10
<212> TYPE: PRT
<213> ORGANISM: Artificial
<220> FEATURE:
<223> OTHER INFORMATION: CDRH1 dAbH1

<400> SEQUENCE: 71

Gly Ile Asp Leu Ser Asn Tyr Ala Ile Asn
1               5                   10

<210> SEQ ID NO 72
<211> LENGTH: 16
<212> TYPE: PRT
<213> ORGANISM: Artificial
<220> FEATURE:
<223> OTHER INFORMATION: CDRH2 dAbH1

<400> SEQUENCE: 72

Ile Ile Trp Ala Ser Gly Thr Thr Phe Tyr Ala Thr Trp Ala Lys Gly
1               5                   10                  15

<210> SEQ ID NO 73
<211> LENGTH: 13
<212> TYPE: PRT
<213> ORGANISM: Artificial
<220> FEATURE:
<223> OTHER INFORMATION: CDRH3 dAbH1

<400> SEQUENCE: 73

Thr Val Pro Gly Tyr Ser Thr Ala Pro Tyr Phe Asp Leu
1               5                   10

<210> SEQ ID NO 74
<211> LENGTH: 12
<212> TYPE: PRT
<213> ORGANISM: Artificial
<220> FEATURE:
<223> OTHER INFORMATION: CDRL1 dAbL1

<400> SEQUENCE: 74

Gln Ser Ser Pro Ser Val Trp Ser Asn Phe Leu Ser
1               5                   10

<210> SEQ ID NO 75
<211> LENGTH: 7
<212> TYPE: PRT
<213> ORGANISM: Artificial
<220> FEATURE:
<223> OTHER INFORMATION: CDRL2 dAbL1

<400> SEQUENCE: 75

Glu Ala Ser Lys Leu Thr Ser
1               5

<210> SEQ ID NO 76
<211> LENGTH: 11
<212> TYPE: PRT
<213> ORGANISM: Artificial
```

<220> FEATURE:
<223> OTHER INFORMATION: CDRL3 dAbL1

<400> SEQUENCE: 76

Gly Gly Gly Tyr Ser Ser Ile Ser Asp Thr Thr
1               5                   10

<210> SEQ ID NO 77
<211> LENGTH: 121
<212> TYPE: PRT
<213> ORGANISM: Artificial
<220> FEATURE:
<223> OTHER INFORMATION: Heavy chain variable domain of anti-albumin
      antibody (no ds)

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 78
<211> LENGTH: 121
<212> TYPE: PRT
<213> ORGANISM: Artificial
<220> FEATURE:
<223> OTHER INFORMATION: Heavy chain variable domain of anti-albumin
      antibody (ds)

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

-continued

```
<210> SEQ ID NO 79
<211> LENGTH: 112
<212> TYPE: PRT
<213> ORGANISM: Artificial
<220> FEATURE:
<223> OTHER INFORMATION: Light chain variable domain of anti-albumin
      antibody (no ds)

<400> SEQUENCE: 79

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Gly Gly Thr Lys Val Glu Ile Lys Arg Thr
            100                 105                 110

<210> SEQ ID NO 80
<211> LENGTH: 112
<212> TYPE: PRT
<213> ORGANISM: Artificial
<220> FEATURE:
<223> OTHER INFORMATION: Light chain variable domain of anti-albumin
      antibody (ds)

<400> SEQUENCE: 80

Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Ser Gly Val Pro Ser Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Gly Tyr Ser Ser Ile
                85                  90                  95

Ser Asp Thr Thr Phe Gly Cys Gly Thr Lys Val Glu Ile Lys Arg Thr
            100                 105                 110
```

MULTISPECIFIC ANTIBODY CONSTRUCTS

CROSS REFERENCE TO RELATED APPLICATIONS

This application is a U.S. national phase of International Application No. PCT/EP2015/064409, filed Jun. 25, 2015, which claims priority to Great Britain Patent Application No. 1411320.3, filed Jun. 25, 2014, incorporated herein by reference in their entirety.

INCORPORATED BY REFERENCE OF MATERIALS SUBMITTED ELECTRONICALLY

Incorporated by reference in its entirety is a computer-readable nucleotide/amino acid sequence listing submitted concurrently herewith and identified as follows: ASCII text file named "51389_SeqListing.txt," 24,883 bytes, created Dec. 16, 2016.

The present disclosure relates to certain multi-specific antibody constructs, pharmaceutical formulations comprising the construct, DNA encoding the constructs and vectors comprising same. The disclosure also extends to a method of expressing the constructs, for example in a host cell and methods for formulating same as a pharmaceutical composition. The disclosure also relates to use of the multi-specific antibody constructs and formulations in treatment.

There are a number of approaches for generating bi-specific antibodies, many of which are based on a format originally described by Morrison et al (Coloma and Morrison 1997, Nat Biotechnol. 15, 159-163) involving the fusion of single chain variable fragments (scFv) to whole antibodies, e.g. IgG, or to antibody Fab fragments, Schoonjans et al., 2000, Journal of Immunology, 165, 7050-7057.

In the case of Fab-scFv, the $V_H$ and $V_L$ domains of the scFvs used in such bi-specific and tri specific molecules are usually held together by peptide linkers. However, for certain combinations of $V_H$ and $V_L$ variable domains, the peptide linkers are unable to confer sufficient stability to the scFv, resulting in variable domain 'breathing' and promiscuous intermolecular pairing with variable domains and thus a tendency to form multimers through the single chain Fv portion thereof. This is illustrated in FIG. 1 in the context of a bispecific molecule.

The present inventors have re-engineered the multi-specific antibody molecules concerned to provide antibody molecules with equivalent functionality, whilst minimizing multimerisation at the expression stage and/or post purification. This facilitates increasing the yield of "monomeric" material obtained and provides molecules of suitable stability for use in treatment after purification, concentration and formulation.

Thus, in one aspect, there is provided a multi-specific antibody molecule comprising or consisting of:

a) a polypeptide chain of formula (I):

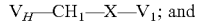
$V_H$—$CH_1$—X—$V_1$; and b) a polypeptide chain of formula (II):

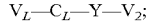
$V_L$—$C_L$—Y—$V_2$;

wherein:
$V_H$ represents a heavy chain variable domain;
$CH_1$ represents a domain of a heavy chain constant region, for example domain 1 thereof;
X represents a bond or linker;
Y represents a bond or linker;
$V_1$ represents a dsFv, a sdAb, a scFv or a dsscFv;
$V_L$ represents a light chain variable domain;
$C_L$ represents a domain from a light chain constant region, such as Ckappa;
$V_2$ represents dsFv, a sdAb, a scFv or a dsscFv;
wherein at least one of $V_1$ or $V_2$ is a dsFv or dsscFv.

Advantageously, the multi-specific antibody molecules of the present disclosure minimize the amount of aggregation seen after purification and maximize the amount of monomer in the formulations of the construct at pharmaceutical concentrations, including maintaining high monomer levels over time upon storage, for example the monomer may be present as 50%, 60%, 70% or 75% or more, such as 80 or 90% or more such as 91, 92, 93, 94, 95, 96, 97, 98 or 99% or more of the total protein.

DETAILED DESCRIPTION OF THE INVENTION

"Multi-specific antibody" as employed herein refers to an antibody molecule as described herein which has two or more binding domains, for example two or three binding domains.

In one embodiment the antibody construct is a tri-specific antibody.

"Tri-specific antibody" as employed herein refers to an antibody molecule with three antigen binding sites, which may independently bind the same or different antigens. In one example a trispecific antibody molecule binds two different antigens, i.e. two binding sites bind the same antigen and the third binding site binds a second, different antigen. Preferably the three binding sites of a trispecific antibody molecule of the invention independently bind three different antigens.

In one embodiment the construct is a bi-specific antibody.

"Bi-specific molecule" as employed herein refers to a molecule with two antigen binding sites, which may bind the same or different antigens.

In one embodiment the domains all bind the same antigen, including binding the same epitope on the antigen or binding different epitopes on the antigen.

In one embodiment there are three binding domains and each of the three binding domains bind different (distinct) antigens.

In one embodiment there are three binding domains and two binding domains bind the same antigen, including binding the same epitope or different epitopes on the same antigen, and the third binding domain binds a different (distinct) antigen.

"Antigen binding site" as employed herein refers to a portion of the molecule, which comprises a pair of variable regions, in particular a cognate pair that interact specifically with the target antigen.

Binding domains as employed herein includes a single domain antibody i.e. a variable region and antigen binding sites.

"Specifically" as employed herein is intended to refer to a binding site or binding domain that only recognizes the antigen to which it is specific or a binding site or binding domain that has significantly higher binding affinity to the antigen to which is specific compared to affinity to antigens to which it is non-specific, for example 5, 6, 7, 8, 9, 10 times higher binding affinity.

Binding affinity may be measured by standard assay, for example surface plasmon resonance, such as BIAcore.

In one embodiment, the multi-specific antibody molecule according to the present disclosure is provided as a dimer of a heavy and light chain of:

Formula (I) and (II) respectively, wherein the $V_H$—$CH_1$ portion together with the $V_L$—$C_L$ portion form a functional Fab or Fab' fragment.

$V_H$ represents a variable domain, for example a heavy chain variable domain. In one embodiment $V_H$ represents a heavy chain variable domain. In one embodiment $V_H$ is a chimeric variable domain, that is to say it comprises components derived from at least two species, for example a human framework and non-human CDRs. In one embodiment $V_H$ is humanized. In one embodiment the $V_H$ is human.

$V_L$ represents a variable domain, for example a light chain variable domain. In one embodiment $V_L$ represents a light chain variable domain. In one embodiment $V_L$ is a chimeric variable domain, that is to say it comprises components derived from at least two species, for example a human framework and non-human CDRs. In one embodiment $V_L$ is humanized. In one embodiment $V_H$ is humanized. In one embodiment the $V_H$ is human Generally $V_H$ and $V_L$ together form an antigen binding domain. In one embodiment $V_H$ and $V_L$ form a cognate pair.

"Cognate pair" as employed herein refers to a pair of variable domains from a single antibody, which was generated in vivo, i.e. the naturally occurring pairing of the variable domains isolated from a host. A cognate pair is therefore a $V_H$ and $V_L$ pair. In one example the cognate pair bind the antigen co-operatively.

"Variable region" as employed herein refers to the region in an antibody chain comprising the CDRs and a framework, in particular a suitable framework.

Variable regions for use in the present disclosure will generally be derived from an antibody, which may be generated by any method known in the art.

"Derived from" as employed herein refers to the fact that the sequence employed or a sequence highly similar to the sequence employed was obtained from the original genetic material, such as the light or heavy chain of an antibody.

"Highly similar" as employed herein is intended to refer to an amino acid sequence which over its full length is 95% similar or more, such as 96, 97, 98 or 99% similar.

Variable regions for use in the present invention, as described herein above for $V_H$ and $V_L$ may be from any suitable source and may be for example, fully human or humanized.

In one embodiment the binding domain formed by $V_H$ and $V_L$ are specific to a first antigen.

In one embodiment the binding domain formed by $V_1$ is specific to a second antigen.

In one embodiment the binding domain formed by $V_2$ is specific to a second or third antigen.

In one embodiment the $CH_1$ domain is a naturally occurring domain 1 from an antibody heavy chain or a derivative thereof.

In one embodiment the $C_L$ fragment, in the light chain, is a constant kappa sequence or a constant lambda sequence or a derivative thereof.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

In one embodiment one or more natural or engineered inter chain (i.e. inter light and heavy chain) disulphide bonds are present in the functional Fab or Fab' fragment.

In one embodiment a "natural" disulfide bond is present between a $CH_1$ and $C_L$ in the polypeptide chains of Formula (I) and (II).

When the $C_L$ domain is derived from either Kappa or Lambda the natural position for a bond forming cysteine is 214 in human cKappa and cLambda (Kabat numbering $4^{th}$ edition 1987).

The exact location of the disulfide bond forming cysteine in $CH_1$ depends on the particular domain actually employed. Thus, for example in human gamma-1 the natural position of the disulfide bond is located at position 233 (Kabat numbering $4^{th}$ edition 1987). The position of the bond forming cysteine for other human isotypes such as gamma 2, 3, 4, IgM and IgD are known, for example position 127 for human IgM, IgE, IgG2, IgG3, IgG4 and 128 of the heavy chain of human IgD and IgA2B.

Optionally there may be a disulfide bond between the $V_H$ and $V_L$ of the polypeptides of formula I and II.

In one embodiment the multi-specific antibody according to the disclosure has a disulfide bond in a position equivalent or corresponding to that naturally occurring between $CH_1$ and $C_L$.

In one embodiment a constant region comprising $CH_1$ and a constant region such as $C_L$ has a disulfide bond which is in a non-naturally occurring position. This may be engineered into the molecule by introducing cysteine(s) into the amino acid chain at the position or positions required. This non-natural disulfide bond is in addition to or as an alternative to the natural disulfide bond present between $CH_1$ and $C_L$. The cysteine(s) in natural positions can be replaced by an amino acid such as serine which is incapable on forming a disulfide bridge.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N.Y., 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagene, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

In one embodiment a disulfide bond between $CH_1$ and $C_L$ is completely absent, for example the interchain cysteines may be replaced by another amino acid, such as serine. Thus in one embodiment there are no interchain disulphide bonds in the functional Fab fragment of the molecule. Disclosures such as WO2005/003170, incorporated herein by reference, describe how to provide Fab fragments without an inter chain disulphide bond.

$V_1$ represents a dsFv, a sdAb, a scFv, or a dsscFv, for example a dsFv, scFv or a dsscFv.

$V_2$ represents a dsFv, a sdAb, a scFv, or a dsscFv, for example a dsFv, scFv or a dsscFv.

In one embodiment, $V_1$ and $V_2$ are both dsscFv.

In one embodiment, $V_1$ and $V_2$ are both dsFv. When both $V_1$ and $V_2$ are dsFv, either the $V_H$ or the $V_L$ variable domains are the same for $V_1$ and $V_2$. In one embodiment, $V_1$ and $V_2$ have the same $V_H$ variable domain. In another embodiment, $V_1$ and $V_2$ have the same $V_L$ variable domain. In one embodiment the $V_H$ and $V_L$ variable domains are the same for $V_1$ and $V_2$. The latter allows for cross-linking which may be desirable for some targets.

In one embodiment $V_1$ is a dsFv and $V_2$ is a scFv. In one embodiment $V_1$ is a scFv and $V_2$ is a dsFv. In one embodiment $V_1$ is a dsscFv and $V_2$ is a dsFv. In one embodiment $V_1$ is a dsFv and $V_2$ is a dsscFv. In one embodiment $V_1$ is a dsscFv and $V_2$ is a scFv. In one embodiment $V_1$ is a scFv and $V_2$ is a dsscFv. In one embodiment, $V_1$ is not a scFv. In one embodiment, $V_2$ is not a scFv. In one embodiment, both $V_1$ and $V_2$ are not scFv.

Thus, in one aspect, there is provided a multi-specific antibody molecule comprising or consisting of:

a) a polypeptide chain of formula (I):

$$V_H\text{—}CH_1\text{—}X\text{—}V_1;\text{ and}$$

b) a polypeptide chain of formula (II):

$$V_L\text{—}C_L\text{—}Y\text{—}V_2;$$

wherein:

$V_H$ represents a heavy chain variable domain;

$CH_1$ represents a domain of a heavy chain constant region, for example domain 1 thereof;

X represents a bond or linker;

Y represents a bond or linker;

$V_1$ represents a dsFv or a dsscFv;

$V_L$ represents a light chain variable domain;

$C_L$ represents a domain from a constant region, for example a light chain constant region domain, such as Ckappa;

$V_2$ represents dsFv or a dsscFv;

"Single chain variable fragment" or "scFv" as employed herein refers to a single chain variable fragment comprising or consisting of a heavy chain variable domain ($V_H$) and a light chain variable domain ($V_L$) which is stabilized by a peptide linker between the $V_H$ and $V_L$ variable domains. The $V_H$ and $V_L$ variable domains may be in any suitable orientation, for example the C-terminus of $V_H$ may be linked to the N-terminus of $V_L$ or the C-terminus of $V_L$ may be linked to the N-terminus of $V_H$.

"Disulphide-stabilized single chain variable fragment" or "dsscFv" as employed herein refers to a single chain variable fragment which is stabilized by a peptide linker between the $V_H$ and $V_L$ variable domain and also includes an inter-domain disulphide bond between $V_H$ and $V_L$.

"Disulphide-stabilized variable fragment" or "dsFv" as employed herein refers to a single chain variable fragment which does not include a peptide linker between the $V_H$ and $V_L$ variable domains and is instead stabilized by an inter-domain disulphide bond between $V_H$ and $V_L$.

"Single domain antibody" or "sdAb" as employed herein refers to an antibody fragment consisting of a single monomeric variable antibody domain, such as $V_H$ or $V_L$ or VHH.

In one embodiment, when $V_1$ and/or $V_2$ are a dsFv or a dsscFv, the disulfide bond between the variable domains $V_H$ and $V_L$ of $V_1$ and/or $V_2$ is between two of the residues listed below (unless the context indicates otherwise Kabat numbering is employed in the list below). Wherever reference is made to Kabat numbering the relevant reference is Kabat et al., 1987, in Sequences of Proteins of Immunological Interest, US Department of Health and Human Services, NIH, USA.

In one embodiment the disulfide bond is in a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100b+V_L49$;

$V_H98+V_L46$ see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995) and a position corresponding thereto in variable region pair located in the molecule.

In one embodiment, the disulphide bond is formed between positions $V_H44$ and $V_L100$.

The amino acid pairs listed above are in the positions conducive to replacement by cysteines such that disulfide bonds can be formed. Cysteines can be engineered into these desired positions by known techniques. In one embodiment therefore an engineered cysteine according to the present disclosure refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N.Y., 1989; Ausbel et al., Current Protocols in Molecular Biology, Greene Publishing & Wiley-Interscience, NY, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Accordingly, in one embodiment when $V_1$ and/or $V_2$ are a dsFv or a dsscFv, the variable domains $V_H$ and $V_L$ of $V_1$ and/or the variable domains $V_H$ and $V_L$ of $V_2$ may be linked by a disulfide bond between two cysteine residues, wherein the position of the pair of cysteine residues is selected from the group consisting of: $V_H37$ and $V_L95$, $V_H44$ and $V_L100$, $V_H44$ and $V_L105$, $V_H45$ and $V_L87$, $V_H100$ and $V_L50$, $V_H100b$ and $V_L49$, $V_H98$ and $V_L46$, $V_H101$ and $V_L46$, $V_H105$ and $V_L43$ and $V_H106$ and $V_L57$.

In one embodiment when $V_1$ and/or $V_2$ are a dsFv or a dsscFv, the variable domains $V_H$ and $V_L$ of $V_1$ and/or the variable domains $V_H$ and $V_L$ of $V_2$ may be linked by a disulfide bond between two cysteine residues, one in $V_H$ and one in $V_L$, which are outside of the CDRs wherein the position of the pair of cysteine residues is selected from the group consisting of $V_H37$ and $V_L95$, $V_H44$ and $V_L100$, $V_H44$ and $V_L105$, $V_H45$ and $V_L87$, $V_H100$ and $V_L50$, $V_H98$ and $V_L46$, $V_H105$ and $V_L43$ and $V_H106$ and $V_L57$.

In one embodiment when $V_1$ is a dsFv or a dsscFv, the variable domains $V_H$ and $V_L$ of $V_1$ are linked by a disulphide bond between two engineered cysteine residues, one at position $V_H44$ and the other at $V_L100$.

In one embodiment when $V_2$ is a dsFv or a dsscFv, the variable domains $V_H$ and $V_L$ of $V_2$ are linked by a disulphide bond between two engineered cysteine residues, one at position $V_H44$ and the other at $V_L100$.

In one embodiment when $V_1$ is a dsFv, a dsscFv, or a scFv, the $V_H$ domain of $V_1$ is attached to X.

In one embodiment when $V_1$ is a dsFv, a dsscFv, or a scFv, the $V_L$ domain of $V_1$ is attached to X.

In one embodiment when $V_2$ is a dsFv, a dsscFv, or a scFv, the $V_H$ domain of $V_2$ is attached to Y.

In one embodiment when $V_2$ is a dsFv, a dsscFv, or a scFv, the $V_L$ domain of $V_2$ is attached to Y.

The skilled person will appreciate that when $V_1$ and/or $V_2$ represents a dsFv, the multi-specific antibody will comprise a third polypeptide encoding the corresponding free $V_H$ or $V_L$ domain which is not attached to X or Y. When $V_1$ and $V_2$ are both a dsFv then the "free variable domain" (i.e. the domain linked to via a disulphide bond to the remainder of the polypeptide) will be common to both chains. Thus whilst the actual variable domain fused or linked via X or Y to the polypeptide may be different in each polypeptide chain the free variable domains paired therewith will generally be identical to each other.

In one embodiment X is a bond.

In one embodiment Y is a bond.

In one embodiment both X and Y are bonds.

In one embodiment X is a linker, preferably a peptide linker, for example a suitable peptide for connecting the portions $CH_1$ and $V_1$.

In one embodiment Y is a linker, preferably a peptide linker, for example a suitable peptide for connecting the portions $C_L$ and $V_2$.

In one embodiment both X and Y are linkers. In one embodiment both X and Y are peptide linkers.

The term "peptide linker" as used herein refers to a peptide comprised of amino acids. A range of suitable peptide linkers will be known to the person of skill in the art.

In one embodiment the peptide linker is 50 amino acids in length or less, for example 20 amino acids or less, such as about 15 amino acids or less, such as 9, 10, 11, 12, 13 or 14 amino acids in length.

In one embodiment the linker is selected from a sequence shown in sequence 1 to 67.

In one embodiment the linker is selected from a sequence shown in SEQ ID NO: 1 or SEQ ID NO: 2.

In one embodiment X has the sequence SGGGGTGGGGS (SEQ ID NO: 1).

In one embodiment Y has the sequence SGGGGTGGGGS (SEQ ID NO: 1).

In one embodiment X has the sequence SGGGGSGGGGS (SEQ ID NO: 2). In one embodiment Y has the sequence SGGGGSGGGGS (SEQ ID NO: 2).

In one embodiment X has the sequence given in SEQ ID NO:1 and Y has the sequence given in SEQ ID NO:2.

In one embodiment X has the sequence given in SEQ ID NO:69 or 70. In one embodiment Y has the sequence given in SEQ ID NO:69 or 70. In one embodiment X has the sequence given in SEQ ID NO:69 and Y has the sequence given in SEQ ID NO:70.

TABLE 1

Hinge linker sequences

| SEQ ID NO: | SEQUENCE |
| --- | --- |
| 3 | DKTHTCAA |
| 4 | DKTHTCPPCPA |
| 5 | DKTHTCPPCPATCPPCPA |
| 6 | DKTHTCPPCPATCPPCPATCPPCPA |
| 7 | DKTHTCPPCPAGKPTLYNSLVMSDTAGTCY |
| 8 | DKTHTCPPCPAGKPTHVNVSVVMAEVDGTCY |
| 9 | DKTHTCCVECPPCPA |
| 10 | DKTHTCPRCPEPKSCDTPPPCPRCPA |
| 11 | DKTHTCPSCPA |

TABLE 2

Flexible linker sequences

| SEQ ID NO: | SEQUENCE |
| --- | --- |
| 12 | SGGGGSE |
| 13 | DKTHTS |
| 14 | (S)GGGGS |
| 15 | (S)GGGGSGGGGS |
| 16 | (S)GGGGSGGGGSGGGGS |
| 17 | (S)GGGGSGGGGSGGGGSGGGGS |
| 18 | (S)GGGGSGGGGSGGGGSGGGGSGGGGS |
| 19 | AAAGSG-GASAS |
| 20 | AAAGSG-XGGGS-GASAS |
| 21 | AAAGSG-XGGGSXGGGS-GASAS |
| 22 | AAAGSG-XGGGSXGGGSXGGGS-GASAS |
| 23 | AAAGSG-XGGGSXGGGSXGGGSXGGGS-GASAS |
| 24 | AAAGSG-XS-GASAS |
| 25 | PGGNRGTTTTRRPATTTGSSPGPTQSHY |
| 26 | ATTTGSSPGPT |
| 27 | ATTTGS |
| - | GS |
| 28 | EPSGPISTINSPPSKESHKSP |
| 29 | GTVAAPSVFIFPPSD |
| 30 | GGGGIAPSMVGGGGS |
| 31 | GGGGKVEGAGGGGGS |
| 32 | GGGGSMKSHDGGGGS |
| 33 | GGGGNLITIVGGGGS |

TABLE 2-continued

Flexible linker sequences

| SEQ ID NO: | SEQUENCE |
|---|---|
| 34 | GGGGVVPSLPGGGGS |
| 35 | GGEKSIPGGGGS |
| 36 | RPLSYRPPFPFGFPSVRP |
| 37 | YPRSIYIRRRHPSPSLTT |
| 38 | TPSHLSHILPSFGLPTFN |
| 39 | RPVSPFTFPRLSNSWLPA |
| 40 | SPAAHFPRSIPRPGPIRT |
| 41 | APGPSAPSHRSLPSRAFG |
| 42 | PRNSIHFLHPLLVAPLGA |
| 43 | MPSLSGVLQVRYLSPPDL |
| 44 | SPQYPSPLTLTLPPHPSL |
| 45 | NPSLNPPSYLHRAPSRIS |
| 46 | LPWRTSLLPSLPLRRRP |
| 47 | PPLFAKGPVGLLSRSFPP |
| 48 | VPPAPVVSLRSAHARPPY |
| 49 | LRPTPPRVRSYTCCPTP- |
| 50 | PNVAHVLPLLTVPWDNLR |
| 51 | CNPLLPLCARSPAVRTFP |

(S) is optional in sequences 14 to 18.

Examples of rigid linkers include the peptide sequences GAPAPAAPAPA (SEQ ID NO: 52), PPPP (SEQ ID NO: 53) and PPP.

In one embodiment the peptide linker is an albumin binding peptide.

Examples of albumin binding peptides are provided in WO2007/106120 and include:

TABLE 3

| SEQ ID NO: | SEQUENCE |
|---|---|
| 54 | DLCLRDWGCLW |
| 55 | DICLPRWGCLW |
| 56 | MEDICLPRWGCLWGD |
| 57 | QRLMEDICLPRWGCLWEDDE |
| 58 | QGLIGDICLPRWGCLWGRSV |
| 59 | QGLIGDICLPRWGCLWGRSVK |
| 60 | EDICLPRWGCLWEDD |
| 61 | RLMEDICLPRWGCLWEDD |
| 62 | MEDICLPRWGCLWEDD |
| 63 | MEDICLPRWGCLWED |
| 64 | RLMEDICLARWGCLWEDD |
| 65 | EVRSFCTRWPAEKSCKPLRG |

TABLE 3-continued

| SEQ ID NO: | SEQUENCE |
|---|---|
| 66 | RAPESFVCYWETICFERSEQ |
| 67 | EMCYFPGICWM |

Advantageously use of albumin binding peptides as a linker may increase the half-life of the multi-specific antibody molecule.

In one embodiment when $V_1$ is a scFv or a dsscFv, there is a linker for example a suitable peptide for connecting the variable domains $V_H$ and $V_L$ of $V_1$.

In one embodiment when $V_2$ is a scFv or a dsscFv, there is a linker for example a suitable peptide for connecting the variable domains $V_H$ and $V_L$ of $V_2$.

In one embodiment the peptide linker in the scFv or dsscFv is in range about 12 to 25 amino acids in length, such as 15 to 20 amino acids.

In one embodiment when $V_1$ is a scFv or a dsscFv, the linker connecting the variable domains $V_H$ and $V_L$ of $V_1$ has the sequence GGGGSGGGGSGGGGSGGGGS (SEQ ID NO: 68).

In one embodiment when $V_2$ is a scFv or a dsscFv, the linker connecting the variable domains $V_H$ and $V_L$ of $V_2$ has the sequence GGGGSGGGGSGGGGSGGGGS (SEQ ID NO: 68).

In one embodiment when $V_1$ is a scFv or a dsscFv, the linker connecting the variable domains $V_H$ and $V_L$ of $V_1$ has the sequence SGGGGSGGGGSGGGGS (SEQ ID NO: 69).

In one embodiment when $V_2$ is a scFv or a dsscFv, the linker connecting the variable domains $V_H$ and $V_L$ of $V_2$ has the sequence SGGGGSGGGGSGGGGS (SEQ ID NO: 69)

In one embodiment when $V_1$ is a scFv or a dsscFv, the linker connecting the variable domains $V_H$ and $V_L$ of $V_1$ has the sequence SGGGGSGGGGTGGGGS (SEQ ID NO: 70).

In one embodiment when $V_2$ is a scFv or a dsscFv, the linker connecting the variable domains $V_H$ and $V_L$ of $V_2$ has the sequence SGGGGSGGGGTGGGGS SEQ ID NO: 70).

Accordingly, in one aspect there is provided a multi-specific antibody molecule, comprising or consisting of:

a) a polypeptide chain of formula (I):

$$V_H\text{—}CH_1\text{—}X\text{—}V_1;\text{ and}$$

b) a polypeptide chain of formula (II):

$$V_L\text{—}C_L\text{—}Y\text{—}V_2;$$

wherein:

$V_H$ represents a heavy chain variable domain;

$CH_1$ represents a domain of a heavy chain constant region, for example domain 1 thereof;

X represents a bond or linker;

Y represents a bond or linker;

$V_1$ represents a dsFv, a sdAb, a scFv or a dsscFv;

$V_L$ represents a light chain variable domain;

$C_L$ represents a domain from a light chain constant region, such as Ckappa;

$V_2$ represents dsFv, a sdAb, a scFv or a dsscFv;

wherein at least one of $V_1$ or $V_2$ is a dsFv or dsscFv.

The present disclosure also provides sequences which are 80%, 90%, 91%, 92%, 93% 94%, 95% 96%, 97%, 98% or 99% similar to a sequence disclosed herein.

"Identity", as used herein, indicates that at any particular position in the aligned sequences, the amino acid residue is identical between the sequences.

"Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains).

Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656,).

Antibodies for use in the multispecific constructs of the present invention may be generated by any suitable method known in the art.

Antibodies generated against an antigen polypeptide may be obtained, where immunization of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Monoclonal antibodies may be prepared by any method known in the art such as the hybridoma technique (Kohler & Milstein, 1975, Nature, 256:495-497), the trioma technique, the human B-cell hybridoma technique (Kozbor et al 1983, Immunology Today, 4:72) and the EBV-hybridoma technique (Cole et al., Monoclonal Antibodies and Cancer Therapy, pp 77-96, Alan R Liss, Inc., 1985).

Antibodies may also be generated using single lymphocyte antibody methods by cloning and expressing immunoglobulin variable region cDNAs generated from single lymphocytes selected for the production of specific antibodies by, for example, the methods described by Babcook, J. et al 1996, Proc. Natl. Acad. Sci. USA 93(15):7843-78481; WO92/02551; WO2004/051268 and WO2004/106377.

The antibodies for use in the present disclosure can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO90/02809; WO91/10737; WO92/01047; WO92/18619; WO93/11236; WO95/15982; WO95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743; 5,969,108, and WO20011/30305.

In one embodiment the multi-specific molecules according to the disclosure are humanized.

Humanized (which include CDR-grafted antibodies) as employed herein refers to molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanized antibodies may optionally further comprise one or more framework residues derived from the non-human species from which the CDRs were derived.

As used herein, the term "humanized antibody molecule" refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the humanized antibody according to the present invention has a variable domain comprising human acceptor framework regions as well as one or more of the CDRs provided herein.

Examples of human frameworks which can be used in the present disclosure are KOL, NEWM, REI, EU, TUR, TEI, LAY and POM (Kabat et al supra). For example, KOL and NEWM can be used for the heavy chain, REI can be used for the light chain and EU, LAY and POM can be used for both the heavy chain and the light chain. Alternatively, human germline sequences may be used; these are available at: http://www2.mrc-lmb.cam.ac.uk/vbase/list2.php.

In a humanized antibody molecule of the present disclosure, the acceptor heavy and light chains do not necessarily need to be derived from the same antibody and may, if desired, comprise composite chains having framework regions derived from different chains.

The framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al 1998, Nature, 332, 323-324). Such changes should be kept to the minimum necessary to recover the affinity of the donor antibody. A protocol for selecting residues in the acceptor framework regions which may need to be changed is set forth in WO91/09967.

Derivatives of frameworks may have 1, 2, 3 or 4 amino acids replaced with an alternative amino acid, for example with a donor residue.

Donor residues are residues from the donor antibody, i.e. the antibody from which the CDRs were originally derived. Donor residues may be replaced by a suitable residue derived from a human receptor framework (acceptor residues).

In one embodiment the multi-specific antibodies of the present disclosure are fully human, in particular one or more of the variable domains are fully human.

Fully human molecules are those in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

In one embodiment the multi-specific antibody molecules of the disclosure are capable of selectively binding two, three or more different antigens of interest.

In one embodiment, antigens of interest bound by the antigen binding domain formed by $V_H/V_L$, or $V_1$ or $V_2$ are independently selected from a cell-associated protein, for example a cell surface protein on cells such as bacterial cells, yeast cells, T-cells, B-cells, endothelial cells or tumour cells, and a soluble protein.

Antigens of interest may also be any medically relevant protein such as those proteins upregulated during disease or infection, for example receptors and/or their corresponding ligands. Particular examples of antigens include cell surface receptors such as T cell or B cell signalling receptors, co-stimulatory molecules, checkpoint inhibitors, natural killer cell receptors, Immunoglobulin receptors, TNFR family receptors, B7 family receptors, adhesion molecules, integrins, cytokine/chemokine receptors, GPCRs, growth factor receptors, kinase receptors, tissue-specific antigens, cancer antigens, pathogen recognition receptors, complement receptors, hormone receptors or soluble molecules such as cytokines, chemokines, leukotrienes, growth factors, hormones or enzymes or ion channels, epitopes, fragments and post translationally modified forms thereof.

In one embodiment the multispecific antibody molecule of the disclosure may be used to functionally alter the activity of the antigen(s) of interest. For example, the antibody fusion protein may neutralize, antagonize or agonise the activity of said antigen, directly or indirectly.

In one embodiment $V_1$ and $V_2$ are specific for the same antigen, for example binding the same or a different epitope therein. In one embodiment $V_1$ is specific for human serum albumin. In one embodiment $V_2$ is specific for human serum albumin. In one embodiment $V_1$ and $V_2$ are specific for two different antigens.

In one embodiment $V_1$ and $V_2$ are specific for the same antigens, for example the same or different epitopes on the same antigen.

In one embodiment, an antigen of interest bound by $V_H/V_L$ or $V_1$ or $V_2$ provides the ability to recruit effector functions, such as complement pathway activation and/or effector cell recruitment.

The recruitment of effector function may be direct in that effector function is associated with a cell, said cell bearing a recruitment molecule on its surface. Indirect recruitment may occur when binding of an antigen to an antigen binding domain (such as $V_1$ or $V_2$) in the molecule according to present disclosure to a recruitment polypeptide causes release of, for example, a factor which in turn may directly or indirectly recruit effector function, or may be via activation of a signalling pathway. Examples include IL2, IL6, IL8, IFNγ, histamine, C1q, opsonin and other members of the classical and alternative complement activation cascades, such as C2, C4, C3-convertase, and C5 to C9.

As used herein, "a recruitment polypeptide" includes a FcγR such as FcγRI, FcγRII and FcγRIII, a complement pathway protein such as, but without limitation, C1q and C3, a CD marker protein (Cluster of Differentiation marker) or a fragment thereof which retains the ability to recruit cell-mediated effector function either directly or indirectly. A recruitment polypeptide also includes immunoglobulin molecules such as IgG1, IgG2, IgG3, IgG4, IgE and IgA which possess effector function.

In one embodiment an antigen binding domain (such as $V_1$ or $V_2$ or $V_H/V_L$) in the multi-specific antibody molecule according to the present disclosure has specificity for a complement pathway protein, with C1q being particularly preferred.

Further, multi-specific antibody molecules of the present disclosure may be used to chelate radionuclides by virtue of a single domain antibody which binds to a nuclide chelator protein. Such fusion proteins are of use in imaging or radionuclide targeting approaches to therapy.

In one embodiment an antigen binding domain within a molecule according to the disclosure (such as $V_1$ or $V_2$ or $V_H/V_L$) has specificity for a serum carrier protein, a circulating immunoglobulin molecule, or CD35/CR1, for example for providing an extended half-life to the antibody fragment with specificity for said antigen of interest by binding to said serum carrier protein, circulating immunoglobulin molecule or CD35/CR1.

As used herein, "serum carrier proteins" include thyroxine-binding protein, transthyretin, al-acid glycoprotein, transferrin, fibrinogen and albumin, or a fragment of any thereof.

As used herein, a "circulating immunoglobulin molecule" includes IgG1, IgG2, IgG3, IgG4, sIgA, IgM and IgD, or a fragment of any thereof.

CD35/CR1 is a protein present on red blood cells which have a half-life of 36 days (normal range of 28 to 47 days; Lanaro et al., 1971, Cancer, 28(3):658-661).

In one embodiment, the antigen of interest for which $V_H/V_L$ has specificity is a serum carrier protein, such as a human serum carrier, such as human serum albumin.

In one embodiment, the antigen of interest for which $V_1$ has specificity is a serum carrier protein, such as a human serum carrier, such as human serum albumin.

In one embodiment, the antigen of interest for which $V_2$ has specificity is a serum carrier protein, such as a human serum carrier, such as human serum albumin.

In one embodiment only one of $V_H/V_L$, $V_1$ or $V_2$ has specificity for a serum carrier protein, such as a human serum carrier, such as human serum albumin.

In one embodiment a binding site in the construct of the present disclosure comprises 6 CDRs, for example SEQ ID NO: 71 for CDRH1, SEQ ID NO: 72 for CDRH2, SEQ ID NO: 73 for CDRH3, SEQ ID NO: 74 for CDRL1, SEQ ID NO: 75 for CDRL2 and SEQ ID NO: 76 for CDRL3.

In one embodiment the said 6 CDRs SEQ ID NO: 71 to 76 are in the position $V_H/V_L$ in the constructs of the present disclosure. In one embodiment the said 6 CDRs SEQ ID NO: 71 to 76 are in the position $V_1$ in the constructs of the present disclosure. In one embodiment the said 6 CDRs SEQ ID NO: 71 to 76 are in the position $V_2$ in the constructs of the present disclosure. In one embodiment the said 6 CDRs SEQ ID NO: 71 to 76 are in the position $V_1$ and $V_2$ in the constructs of the present disclosure. In one embodiment the said 6 CDRs SEQ ID NO: 71 to 76 are in the position $V_H/V_L$ and $V_1$ in the constructs of the present disclosure. In one embodiment the said 6 CDRs SEQ ID NO: 71 to 76 are in the position $V_H/V_L$ and $V_2$ in the constructs of the present disclosure.

In one embodiment the albumin binding site in a construct of the present disclosure comprises a heavy variable domain selected from SEQ ID NO: 77 and SEQ ID NO: 78 and a light chain variable domain selected from SEQ ID NO: 79 and SEQ ID NO: 80, in particular SEQ ID NO: 77 and 79 or SEQ ID NO: 78 and 80 for the heavy and light chain respectively. In one embodiment these domains are in the position $V_H/V_L$ in the constructs of the present disclosure. In one embodiment these variable domains are in the position $V_1$. In one embodiment these variable domains are in the position $V_2$. In one embodiment these variable domains are in the position $V_1$ and $V_2$. In one embodiment these variable domains are in the position $V_H/V_L$ and $V_1$ in the constructs of the present disclosure. In one embodiment these variable domains are in the position $V_H/V_L$ and $V_2$ in the constructs of the present disclosure. When the variable domains are in two locations in the constructs of the present disclosure the same pair of variable domains may be in each location or two different pairs of variable domains may be employed.

In one embodiment the multi-specific antibody molecules of the present disclosure are processed to provide improved affinity for a target antigen or antigens. Such variants can be obtained by a number of affinity maturation protocols including mutating the CDRs (Yang et al J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al Nature, 391, 288-291, 1998). Vaughan et al (supra) discusses these methods of affinity maturation.

Improved affinity as employed herein in this context refers to an improvement over the starting molecule.

If desired a multispecific antibody construct for use in the present disclosure may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al Controlled Drug Delivery, 2nd Ed., Robinson et al eds., 1987, pp. 623-53; Thorpe et al 1982, Immunol. Rev., 62:119-58 and Dubowchik et al 1999, Pharmacology and Therapeutics, 83, 67-123). Particular chemical procedures include, for example, those described in WO93/06231, WO92/22583, WO89/00195, WO89/01476 and WO03031581. Alternatively, where the effector molecule is a protein or polypeptide the linkage may be achieved using recombinant DNA procedures, for example as described in WO86/01533 and EP0392745.

The term "effector molecule" as used herein includes, for example, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Other effector molecules may include chelated radionuclides such as 111In and 90Y, Lu177, Bismuth213, Californium252, Iridium192 and Tungsten188/Rhenium188; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, pseudomonas exotoxin, or diphtheria toxin, a protein such as insulin, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741, 900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include 125I, 131I, 111In and 99Tc.

In another embodiment the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one embodiment antibodies for use in the present disclosure are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. Nos. 5,219,996; 5,667,425; WO98/25971, WO2008/038024). In one embodiment the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment, a F(ab')$_2$, Fab or Fab' in the molecule is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one embodiment PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

Particular PEG molecules include 2-[3-(N-maleimido)propionamido]ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

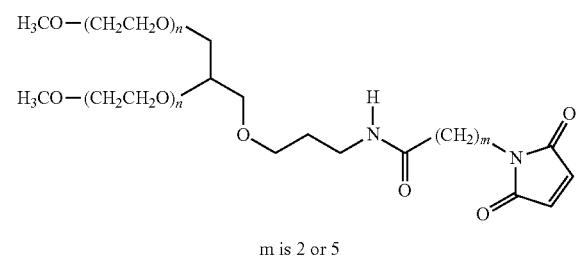

m is 2 or 5

That is to say each PEG is about 20,000 Da.

Further alternative PEG effector molecules of the following type:

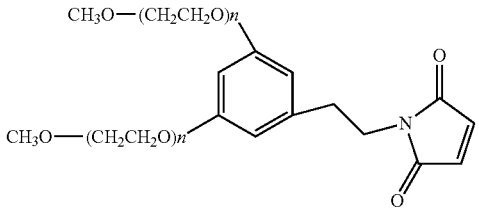

are available from Dr Reddy, NOF and Jenkem.

In one embodiment there is provided an antibody molecule which is PEGylated (for example with a PEG described herein), attached through a cysteine amino acid residue at or about amino acid 226 in the chain, for example amino acid 226 of the heavy chain (by sequential numbering).

In one embodiment there is provided a polynucleotide sequence encoding a molecule of the present disclosure, such as a DNA sequence.

In one embodiment there is provided a polynucleotide sequence encoding one or more, such as two or more, or three or more polypeptide components of a molecule of the present disclosure, for example:

a) a polypeptide chain of formula (I):

$$V_H-CH_1-X-V_1; \text{ and}$$

b) a polypeptide chain of formula (II):

$$V_L-C_L-Y-V_2;$$

wherein:
$V_H$ represents a heavy chain variable domain;
$CH_1$ represents a domain of a heavy chain constant region, for example domain 1 thereof;
X represents a bond or linker;
Y represents a bond or linker;
$V_1$ represents a dsFv, a sdAb, a scFv or a dsscFv;
$V_L$ represents a light chain variable domain;
$C_L$ represents a domain from a light chain constant region, such as Ckappa;
$V_2$ represents dsFv, a sdAb, a scFV or a dsscFv;
wherein at least one of $V_1$ or $V_2$ is a dsFv or dsscFv.

In one embodiment the polynucleotide, such as the DNA is comprised in a vector.

The skilled person will appreciate that when $V_1$ and/or $V_2$ represents a dsFv, the multi-specific antibody will comprise a third polypeptide encoding the corresponding free $V_H$ or $V_L$ domain which is not attached to X or Y. Accordingly the multispecific protein of the present invention may be encoded by one or more, two or more or three or more polynucleotides and these may be incorporated into one or more vectors.

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding a multispecific protein of the present invention. Any suitable host cell/vector system may be used for expression of the DNA sequences encoding the antibody molecule of the present invention. Bacterial, for example E. coli, and other microbial systems may be used or eukaryotic, for example mammalian, host cell expression systems may also be used. Suitable mammalian host cells include CHO, myeloma, NSO myeloma cells and SP2 cells, COS cells or hybridoma cells.

The present disclosure also provides a process for the production of a multispecific protein according to the present disclosure comprising culturing a host cell containing a vector of the present invention under conditions suitable for leading to expression of protein from DNA encoding the multispecific protein of the present invention, and isolating the multispecific protein.

For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides. In one example the cell line may be transfected with two vectors, each encoding a polypeptide chain of an antibody molecule of the present invention. Where $V_1$ and/or $V_2$ are a dsFv the cell line may be transfected with three vectors, each encoding a polypeptide chain of a multispecific protein of the invention.

In one embodiment the cell line is transfected with two vectors each one encoding a different polypeptide selected from:

a) a polypeptide chain of formula (I):

$$V_H-CH_1-X-V_1;$$

b) a polypeptide chain of formula (II):

$$V_L-C_L-Y-V_2;$$

wherein:
$V_H$ represents a heavy chain variable domain;
$CH_1$ represents a domain of a heavy chain constant region, for example domain 1 thereof;
X represents a bond or linker;
Y represents a bond or linker;
$V_1$ represents a dsFv, a sdAb, a scFv or a dsscFv;
$V_L$ represents a light chain variable domain;
$C_L$ represents domain from a light chain constant region, such as Ckappa;
$V_2$ represents dsFv, a sdAb, a scFV or a dsscFv;
wherein at least one of $V_1$ or $V_2$ is a dsFv or dsscFv.

In one embodiment when $V_1$ is a dsFv and the $V_H$ domain of $V_1$ is attached to X, the cell line may be transfected with a third vector which encodes the $V_L$ domain of $V_1$.

In one embodiment when $V_1$ is a dsFv and the $V_L$ domain of $V_1$ is attached to X, the cell line may be transfected with a third vector which encodes the $V_H$ domain of $V_1$.

In one embodiment when $V_2$ is a dsFv and the $V_H$ domain of $V_2$ is attached to Y, the cell line may be transfected with a third vector which encodes the $V_L$ domain of $V_2$.

In one embodiment when $V_2$ is a dsFv and the $V_L$ domain of $V_2$ is attached to Y, the cell line may be transfected with a third vector which encodes the $V_H$ domain of $V_2$.

In one embodiment when both $V_1$ and $V_2$ are a dsFv and the $V_L$ domain of $V_2$ is attached to Y and the $V_L$ domain of $V_1$ is attached to X, the cell line may be transfected with a third vector which encodes the common $V_H$ domain of both $V_1$ and $V_2$.

In one embodiment when both $V_1$ and $V_2$ are a dsFv and the $V_H$ domain of $V_2$ is attached to Y and the $V_H$ domain of $V_1$ is attached to X, the cell line may be transfected with a third vector which encodes the common $V_L$ domain of both $V_1$ and $V_2$.

It will be appreciated that the ratio of each vector transfected into the host cell may be varied in order to optimize expression of the multi-specific antibody product. In one embodiment where two vectors are used the ratio of vectors may be 1:1. In one embodiment where three vectors are used the ratio of vectors may be 1:1:1. It will be appreciated that the skilled person is able to find an optimal ratio by routine testing of protein expression levels following transfection. Alternatively or in addition, the levels of expression of each polypeptide chain of the multi-specific construct from each vector may be controlled by using the same or different promoters.

It will be appreciated that two or more or where present, three of the polypeptide components may be encoded by a polynucleotide in a single vector. It will also be appreciated that where two or more, in particular three or more, of the polypeptide components are encoded by a polynucleotide in a single vector the relative expression of each polypeptide component can be varied by utilizing different promoters for each polynucleotide encoding a polypeptide component of the present disclosure.

In one embodiment the vector comprises a single polynucleotide sequence encoding two or where present, three, polypeptide chains of the multispecific antibody molecule of the present invention under the control of a single promoter.

In one embodiment the vector comprises a single polynucleotide sequence encoding two, or where present, three, polypeptide chains of the multispecific antibody molecule of the present disclosure wherein each polynucleotide sequence encoding each polypeptide chain is under the control of a different promoter.

The multispecific proteins according to the present disclosure are expressed at good levels from host cells. Thus the properties of the antibodies and/or fragments appear to be optimized and conducive to commercial processing.

Advantageously, the multi-specific antibody molecules of the present disclosure minimize the amount of aggregation seen after purification and maximize the amount of monomer in the formulations of the construct at pharmaceutical concentrations, for example the monomer may be present as 50%, 60%, 70% or 75% or more, such as 80 or 90% or more such as 91, 92, 93, 94, 95, 96, 97, 98 or 99% or more of the total protein. In one example, a purified sample of a multi-specific antibody molecule of the present disclosure remains greater than 98% or 99% monomeric after 28 days storage at 4° C. In one example, a purified sample of a multi-specific antibody molecule of the present disclosure at 5 mg/ml in phosphate buffered saline (PBS) remains greater than 98% monomeric after 28 days storage at 4° C.

The antibody molecules of the present disclosure and compositions comprising the same are useful in the treatment, for example in the treatment and/or prophylaxis of a pathological condition. The present disclosure also provides a pharmaceutical or diagnostic composition comprising an antibody molecule of the present disclosure in combination with one or more of a pharmaceutically acceptable excipient, diluent or carrier. Accordingly, provided is the use of an antibody of the present disclosure for use in treatment and for the manufacture of a medicament, in particular for an indication disclosed herein.

The composition will usually be supplied as part of a sterile, pharmaceutical composition that will normally include a pharmaceutically acceptable carrier. A pharmaceutical composition of the present disclosure may additionally comprise a pharmaceutically-acceptable adjuvant.

The present disclosure also provides a process for preparation of a pharmaceutical or diagnostic composition comprising adding and mixing the antibody molecule of the present disclosure together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent.

The pharmaceutical compositions suitably comprise a therapeutically effective amount of the antibody molecule of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Alternatively, the dose may be 1 to 500 mg per day such as 10 to 100, 200, 300 or 400 mg per day. Pharmaceutical compositions may be conveniently presented in unit dose forms containing a predetermined amount of an active agent of the invention.

Compositions may be administered individually to a patient or may be administered in combination (e.g. simultaneously, sequentially or separately) with other agents, drugs or hormones.

The dose at which the antibody molecule of the present disclosure is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half-life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolized macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

In one embodiment, in formulations according to the present disclosure, the pH of the final formulation is not similar to the value of the isoelectric point of the antibody or fragment, for if the pH of the formulation is 7 then a pI of from 8-9 or above may be appropriate. Whilst not wishing to be bound by theory it is thought that this may ultimately provide a final formulation with improved stability, for example the antibody or fragment remains in solution.

The pharmaceutical compositions of this disclosure may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared. Preferably the antibody molecules of the present invention are administered subcutaneously, by inhalation or topically.

Direct delivery of the compositions will generally be accomplished by injection, subcutaneously, intraperitoneally, intravenously or intramuscularly, or delivered to the interstitial space of a tissue. The compositions can also be administered into a specific tissue of interest. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases (such as nebulisable solutions or suspensions). Inhalable powders according to the disclosure containing the active substance may consist solely of the abovementioned active substances or of a mixture of the above mentioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 µm, in particular from 1 to 5 µm. The particle size of the active agent (such as the antibody or antibody fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilizers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

In one embodiment the formulation is provided as discrete ampoules containing a unit dose for delivery by nebulisation.

In one embodiment the antibody is supplied in lyophilised form, for reconstitutions or alternatively as a suspension formulation.

The antibody of the present disclosure can be delivered dispersed in a solvent, e.g., in the form of a solution or a suspension. It can be suspended in an appropriate physiological solution, e.g., physiological saline, a pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. As mentioned supra a suspension can made, for example, from lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent solution used for the formulation, aseptic suspension of the antibody in the sterile buffered solvent solution, and dispensing of the formulation into sterile receptacles by methods familiar to those of ordinary skill in the art.

Nebulisable formulation according to the present disclosure may be provided, for example, as single dose units (e.g., sealed plastic containers or vials) packed in foil envelopes. Each vial contains a unit dose in a volume, e.g., 2 ml, of solvent/solution buffer.

The antibodies of the present disclosure are thought to be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The pathological condition or disorder, may, for example be selected from the group consisting of infections (viral, bacterial, fungal and parasitic), endotoxic shock associated with infection, arthritis such as rheumatoid arthritis, asthma such as severe asthma, chronic obstructive pulmonary disease (COPD), pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia.

The present disclosure also provides a multi-specific antibody molecule according to the present invention for use in the treatment or prophylaxis of pain, particularly pain associated with inflammation.

Thus there is provided a multi-specific antibody according to the present disclosure for use in treatment and methods of treatment employing same.

In one embodiment there is provided a process for purifying a multi-specific antibody (in particular an antibody or fragment according to the invention).

In one embodiment there is provided a process for purifying a multi-specific antibody (in particular an antibody or fragment according to the invention) comprising the steps: performing anion exchange chromatography in non-binding mode such that the impurities are retained on the column and the antibody is maintained in the unbound fraction. The step may, for example be performed at a pH about 6-8.

The process may further comprise an initial capture step employing cation exchange chromatography, performed for example at a pH of about 4 to 5.

The process may further comprise of additional chromatography step(s) to ensure product and process related impurities are appropriately resolved from the product stream.

The purification process may also comprise of one or more ultra-filtration steps, such as a concentration and diafiltration step.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400 µg per mg of antibody product or less such as 100 µg per mg or less, in particular 20 µg per mg, as appropriate.

The antibody molecule of the present invention may also be used in diagnosis, for example in the in vivo diagnosis and imaging of disease states.

In one embodiment there is provided a method of selecting a multi-specific protein construct according to the present invention comprising:
  a) determining the yield of monomeric multi-specific protein when either $V_1$ or $V_2$ is a dsscFv for a given variable region pair
  b) determining the yield of monomeric multi-specific protein when whichever of $V_1$ or $V_2$ was tested in (a) is a dsFv for the same variable region pair and
  c) comparing the yield of monomer obtained in (a) and (b) and selecting the multi-specific protein with the highest monomeric yield.

Typically the "variable region pair" in step (a) and (b) of the method are a $V_H$ and $V_L$ pair. Generally $V_H$ and $V_L$ together form an antigen binding domain, $V_1$ or $V_2$. The method therefore allows the $V_H$ and $V_L$ pair to be tested as both a dsscFv and a dsFv in the constructs of the present invention and the most monomeric construct is selected in step (c).

Typically in step (a) and (b) of the method the yield is determined following purification, such as following affinity chromatography. Monomer yield may be determined using any suitable method, such as size exclusion chromatography.

"Comprising" in the context of the present specification is intended to meaning including. Where technically appropriate, embodiments of the invention may be combined. Embodiments are described herein as comprising certain features/elements. The disclosure also extends to separate embodiments consisting or consisting essentially of said features/elements.

Technical references such as patents and applications are incorporated herein by reference. Any embodiments specifically and explicitly recited herein may form the basis of a disclaimer either alone or in combination with one or more further embodiments.

The present disclosure is further described by way of illustration only in the following examples, which refer to the accompanying Figures, in which:

BRIEF DESCRIPTION OF THE FIGURES

FIG. 1 shows the Fab-2×dsscFv and Fab-dsscFv-dsFv constructs of the present disclosure.

FIG. 3 shows G3000 SE HPLC analysis of protein G-purified, HEK293-expressed Fab-1×dsscFv, 1×scFv and Fab-2×dsscFv proteins FIG. 4 SDS-PAGE analysis of purified, HEK293-expressed Fab-2×dsscFv #3 proteins FIG. 5 S200 SE HPLC analysis of purified, HEK293-expressed Fab-2×dsscFv #3 proteins FIG. 6 shows SDS-PAGE analysis of various protein G purified Fab-dsscFv-dsFv constructs of the present disclosure.
(A) Fab-dsscFv-dsscFv samples. (B) Fab-dsscFv-dsFv samples FIG. 7 shows G3000 SE HPLC analysis of protein G-purified Fab-dssFv-dsFv constructs of the present disclosure.

FIG. 8 shows SDS-PAGE analysis of various constructs according to the present disclosure under reducing conditions.

FIG. 10 shows SDS-Page analysis of protein-G purified EXPiHEK expressed Fab-2×scFv and Fab-2×dsscFv formats

EXAMPLES

Figure 2:
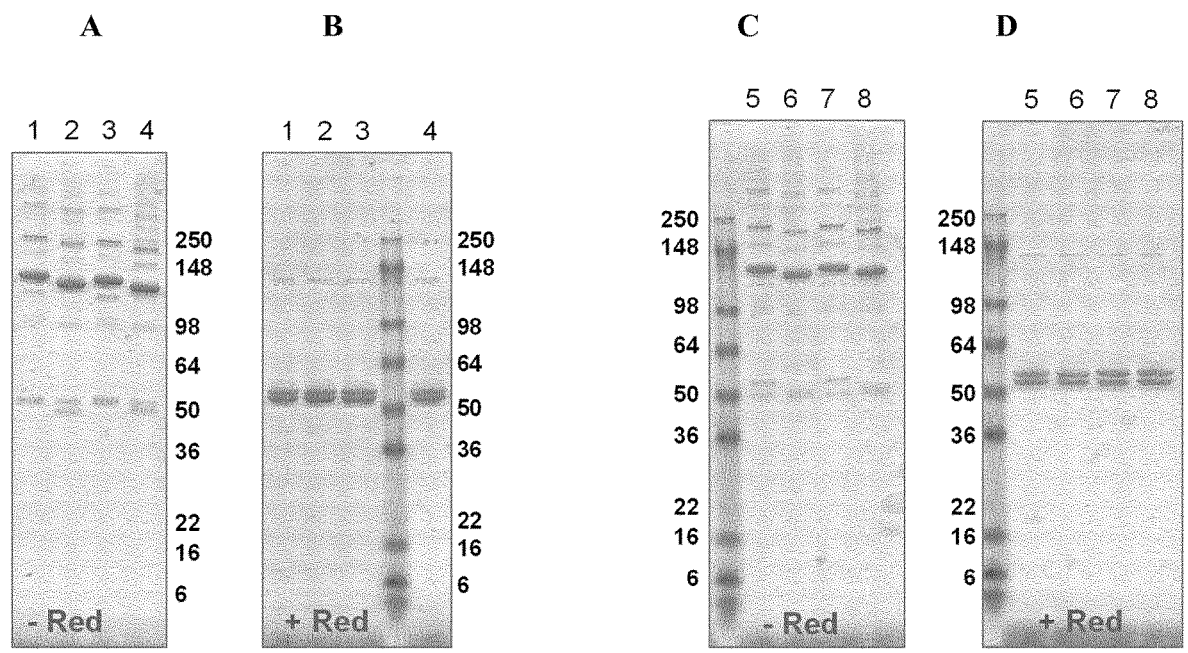
FIG. 2 shows SDS-PAGE analysis of protein G-purified, HEK293-expressed Fab-1×dsscFv, 1×scFv and Fab-2×dsscFv proteins.

Antibody fragments to ANTIGEN 1 are labelled #1
Antibody fragments to ANTIGEN 2 are labelled #2
Antibody fragments to ANTIGEN 3 are labelled #3
Antibody fragments to ANTIGEN 4 are labelled #4

Example 1

Fab-2×dsscFv

Construction of Plasmids for Expression in Mammalian Cells

Plasmids for the expression of Fab #2-(HC)dsscFv #3, (LC)dsscFv #4 and Fab #2-(LC)dsscFv #3,(HC)dsscFv #4 (see FIG. 1), were constructed by fusing scFv #3 and scFv #4 to the C-terminus of the Km3 allotype human kappa constant region of the #2 light chain using the flexible linker SGGGGSGGGGS [also referred herein as S, 2×G4S] (SEQ ID NO: 2), or by fusing scFv #3 and scFv #4 to the C-terminus of the, γ1 isotype human gamma-1 CH$_1$ constant region of the #2 heavy chain using the flexible linker SGGGGTGGGGS [also referred to herein as S, G4T, G4S] (SEQ ID NO: 1). In addition, point mutations were introduced into the DNA sequences at selected residues in the framework region of both vL #3/vL #4 and vH #3/vH #4. The mutations (heavy chain G44C and light chain G100C) were introduced to create an interchain disulphide bond between the heavy and light chains of the Fv #3. The mutations (heavy chain G44C and light chain Q100C) were introduced to create an interchain disulphide bond between the heavy and light chains of the Fv #4.

Gene fragments encoding scFv #4 and dsscFv #4 (vHvL and vLvH orientation) were manufactured chemically and fused to Fab #2 as detailed above to generate:

```
Plasmid e1:
Light#2-(SGGGGSGGGGS [SEQ ID NO: 2])-vL#4-
(GGGGSGGGGSGGGGSGGGGS [SEQ ID NO 68])-vH#4;

Plasmid f1:
Light#2-(SGGGGSGGGGS [SEQ ID NO: 2])-dsvL#4-
(GGGGSGGGGSGGGGSGGGGS [SEQ ID NO: 68])-dsvH#4;

Plasmid e2:
Light#2-(SGGGGSGGGGS [SEQ ID NO: 2])-vH#4-
(GGGGSGGGGSGGGGSGGGGS [SEQ ID NO: 68])-vL#4;

Plasmid f2:
Light#2-(SGGGGSGGGGS [SEQ ID NO: 2])-dsvH#4-
(GGGGSGGGGSGGGGSGGGGS [SEQ ID NO: 68])-dsvL#4;

Plasmid g1
Heavy#2-(SGGGGTGGGGS [SEQ ID NO: 1])-vL#4-
(GGGGSGGGGSGGGGSGGGGS [SEQ ID NO: 68])-vH#4;

Plasmid h1:
Heavy#2-(SGGGGTGGGGS [SEQ ID NO: 1])-dsvL#4-
(GGGGSGGGGSGGGGSGGGGS [SEQ ID NO: 68])-dsvH#4;

Plasmid g2:
Heavy#2-(SGGGGTGGGGS [SEQ ID NO: 1])-vH#4-
(GGGGSGGGGSGGGGSGGGGS [SEQ ID NO: 68])-vL#4;
and Plasmid h2:
Heavy#2-(SGGGGTGGGGS [SEQ ID NO: 1])-dsvH#4-
(GGGGSGGGGSGGGGSGGGGS [SEQ ID NO: 68])-dsvL#4.

pND1 plasmid
(Fab#2 Heavy-(SGGGGTGGGGS SEQ ID NO: 1)-dsvH#3-
(GGGGSGGGGSGGGGSGGGGS SEQ ID NO: 68)-dsvL#3)
```

[Plasmid i] was already available.

The gene fragment encoding dsHLscFv #3 was excised from pND1 and fused to light chain #2 as detailed above to generate:

```
Light#2-(SGGGGSGGGGS SEQ ID NO: 2)-dsvH#3-
(GGGGSGGGGSGGGGSGGGGS SEQ ID NO: 68)-
dsvL#3 [Plasmid j].
```

All Fab fusion formats were cloned into mammalian expression vectors under the control of the HCMV-MIE promoter and SV40E polyA sequence.

HEK293 Expression of Fab-1×dsscFv-1×scFv and Fab-2× dsscFv Formats

HEK293 cells were transfected with the relevant plasmids using Invitrogen's 293fectin transfection reagent according to the manufacturer's instructions. Plasmids were mixed as shown in Table 4 to express the different constructs:

TABLE 4

| Antibody Construct | Plasmids used |
| --- | --- |
| Fab#2-(HC)dsHLscFv#3, (LC)HLscFv#4 | 1. Plasmid e2<br>2. Plasmid i |
| Fab#2-(HC)dsHLscFv#3, (LC)dsHLscFv#4 | 1. Plasmid f2<br>2. Plasmid i |
| Fab#2-(HC)dsHLscFv#3, (LC)LHscFv#4 | 1. Plasmid e1<br>2. Plasmid i |
| Fab#2-(HC)dsHLscFv#3, (LC)dsLHscFv#4 | 1. Plasmid f1<br>2. Plasmid i |
| Fab#2-(LC)dsHLscFv#3, (HC)HLscFv#4 | 1. Plasmid g2<br>2. Plasmid j |
| Fab#2-(LC)dsHLscFv#3, (HC)dsHLscFv#4 | 1. Plasmid h2<br>2. Plasmid j |
| Fab#2-(LC)dsHLscFv#3, (HC)LHscFv#4 | 1. Plasmid g1<br>2. Plasmid j |
| Fab#2-(LC)dsHLscFv#3, (HC)dsLHscFv#4 | 1. Plasmid h1<br>2. Plasmid j |

The ratio of the plasmids used for the transfections was 1:1. A total of 50 µg plasmid DNA was incubated with 125 µl 293fectin+4.25 ml Optimem media for 20 mins at RT. The mixture was then added to 50 ml HEK293 cells in suspension at $1 \times 10^6$ cells/ml and incubated with shaking at 37° C. Supernatants were harvested on day 10 by centrifugation at 1500 g to remove cells and the supernatant was passed through a 0.22 µm filter. Expression level was determined by Protein-G HPLC.

Table 5 shows the results of the Protein-G HPLC assay. As can be seen, the levels of expression of all the constructs were comparable to each other, covering a range of 11-23 µg/ml. Those denoted with an asterisk (*) were expressed in a separate transfection, therefore the absolute expression levels of LC-scFv #3,HC-scFv #4 cannot be compared with HC-scFv #3,LC-scFv #4.

TABLE 5

| Antibody Construct | Expression level (µg/ml) |
| --- | --- |
| Fab#2(HC)dsHLscFv#3, (LC)HLscFv#4 | 23 |
| Fab#2(HC)dsHLscFv#3, (LC)dsHLscFv#4 | 18 |
| Fab#2(HC)dsHLscFv#3, (LC)LHscFv#4 | 21 |
| Fab#2(HC)dsHLscFv#3, (LC)dsLHscFv#4 | 20 |
| Fab#2(LC)dsHLscFv#3, (HC)HLscFv#4 | 13* |
| Fab#2(LC)dsHLscFv#3, (HC)dsHLscFv#4 | 12* |
| Fab#2(LC)dsHLscFv#3, (HC)LHscFv#4 | 12* |
| Fab#2(LC)dsHLscFv#3, (HC)dsLHscFv#4 | 11* |

Protein-G Purification of HEK293 Expressed Fab-1×dsscFv-1×scFv and Fab-2×dsscFv Formats The ~50 ml HEK293 supernatants were concentrated ~25 fold to ~2 ml using 10 kDa molecular weight cut off centrifugation concentrators. The concentrated supernatants were applied to a 1 ml HiTrap Protein-G FF column (GE Healthcare) equilibrated in 20 mM phosphate, 40 mM NaCl pH 7.4. The column was washed with 20 mM phosphate, 40 mM NaCl pH 7.4 and the bound material was eluted with 0.1M glycine/HCl pH 2.7. The elution peak was collected and pH adjusted to ~pH 7.0 with 2M Tris/HCl pH 8.5. The pH adjusted elutions were concentrated and buffer exchanged into PBS pH 7.4 using 10 kDa molecular weight cut off centrifugation concentrators.

SDS-PAGE Analysis of Protein-G Purified, HEK293 Expressed Fab-1×dsscFv-1×scFv and Fab-2×dsscFv Formats Samples (2 µg) were diluted with PBS to a volume of 9.75 µl to which 3.75 µl 4×LDS sample buffer and 1.5 µl 100 mM N-ethylmaleimide (non-reduced samples) or 1.5 µl 10× NuPAGE reducing agent (reduced samples) was added. The samples were vortexed, incubated at 70° C. for 10 minutes, cooled and centrifuged at 12500 rpm for 30 seconds. The prepared samples were loaded onto a 4-20% acrylamide Tris/Glycine SDS gel and run for ~100 minutes at 125V, constant voltage. SeeBluePlus2 (Life Technologies) molecular weight ladder was used. The gels were stained with Instant Blue protein stain (Expedeon) and destained with distilled water.

The expected band sizes after reducing and non-reducing SDS-PAGE are indicated in Table 6.

TABLE 6

Expected band sizes after SDS-PAGE (kDa)
(H = heavy chain, L = light chain, +/− reducing agent)

| | −Red | +Red | | −Red | +Red |
| --- | --- | --- | --- | --- | --- |
| Fab-1xdsscFv, 1x scFv | ~100 | H~50<br>L~50 | Fab-2xdsscFv | ~100 | H~50<br>L~50 |

For all proteins, the non-reducing gel was expected to show a band at ~100 kDa, whilst the reducing gels were expected to show a doublet at ~50 kDa with equal staining in the both bands.

For all Fab-1×dsscFv-1×scFv and Fab-2×dsscFv proteins, the reducing SDS-PAGE gels showed banding patterns which indicated that the constructs were being expressed correctly in terms of both migration position and staining intensity with a doublet at ~50 kDa (FIG. 2B,D). The additional uppermost minor band is consistent with non-reduced full-length protein. As expected, disulphide linked multimers are seen on the non-reducing gel (FIG. 2A,C), which disappear under reducing conditions (FIG. 2B,D). The minor bands at ~50 kDa on the non-reducing gel (FIG. 2A,C) may be consistent with incomplete ds bond formation between the heavy and light chain in the Fab region.

G3000 SE-HPLC Analysis of Protein-G Purified, HEK293 Expressed Fab-1×dsscFv-1×scFv and Fab-2×dsscFv Formats 10 µg purified protein samples (100 µl of 0.1 mg/ml stock diluted in PBS) were injected onto a TSK Gel G3000SWXL, 7.8×300 mm, column (Tosoh) 3 days post-purification and developed with an isocratic gradient of 200 mM phosphate pH 7.0 at 1 ml/min. Signal detection was by absorbance at 280 nm.

The results are shown in FIG. 3. As can be seen from FIG. 3, after Protein-G purification, the Fab-1×dsscFv-1×scFv and Fab-2×dsscFv formats were 83-89% monomer.

Although all the samples have similar monomer levels in the assay, those samples that contain a scFv lacking the Fv disulphide are in a dynamic equilibrium. This means the % monomer measured in the assay for these samples is dependent on the concentration of the sample, more concentrated samples give higher % monomer and less concentrated samples give lower % monomer. In contrast the samples where both scFv contain a disulphide are stable and are not in dynamic equilibrium. Therefore the % monomer measured in the assay does not change with changes in the sample concentration.

As the monomers and multimers in the Fab-2×dsscFv formats are stable and not in a dynamic equilibrium the samples can be easily further purified to increase the % monomer. The purified monomeric samples will also remain monomeric even when the concentration of the construct in a given formulation is increased, thereby making the constructs very suitable for use in pharmaceutical preparations. In contrast, Fab-2×scFv can after purification as monomer be subject to intermolecular dynamic domain exchange between the vL and vH of the scFv domains. In addition therefore to increased risk of formation of dimer, trimer, higher order structures and aggregate such molecules are difficult to observe since non-aggregated forms can resolve to monomer after dilution steps which are used during analytical methods. Hence, Fab-2×dsscFv provide additional clarity during analysis of pharmaceutical compositions.

CHOS Expression of Fab-1×dsscFv-1×scFv and Fab-2×dsscFv Formats

CHOS cells were transfected with the relevant plasmids by electroporation methods at 1 L scale. Plasmids were mixed as shown in Table 7 to express the protein. Cultures were grown in CD-CHO medium supplemented with 2 mM GlutaMAX and incubated at 37° C. with 8% $CO_2$ at 140 rpm for 24 h and subsequently incubated for a further 13 days at 32° C. At day 4 post-transfection, sodium butyrate at a final concentration of 3 mM was added to the culture. On day 14 post-transfection, culture supernatants were harvested by centrifugation and 0.22 µm filter sterilized. Expression titres were measured by Protein G HPLC (Table 8).

TABLE 7

| Antibody Construct | Plasmids used | |
|---|---|---|
| Fab#2-(LC)dsHLscFv#3, (HC)HLscFv#4 | 3. Plasmid g2 | 1. Plasmid j |
| Fab#2-(LC)dsHLscFv#3, (HC)dsHLscFv#4 | 3. Plasmid h2 | 1. Plasmid j |
| Fab#2-(LC)dsHLscFv#3, (HC)LHscFv#4 | 3. Plasmid g1 | 1. Plasmid j |
| Fab#2-(LC)dsHLscFv#3, (HC)dsLHscFv#4 | 3. Plasmid h1 | 1. Plasmid j |

TABLE 8

| Antibody Construct | Expression level (µg/ml) |
|---|---|
| Fab#2-(LC)dsHLscFv#3, (HC)HLscFv#4 | 15 |
| Fab#2-(LC)dsHLscFv#3, (HC)dsHLscFv#4 | 17 |
| Fab#2-(LC)dsHLscFv#3, (HC)LHscFv#4 | 18 |
| Fab#2-(LC)dsHLscFv#3, (HC)dsLHscFv#4 | 16 |

Protein-G Purification of CHO Expressed Fab-1×dsscFv-1×scFv and Fab-2×dsscFv Formats The 1 L CHO supernatants were concentrated ~25 fold to ~40 ml using a 10 kDa molecular weight cut off Amicon stirred cell. The concentrated supernatants were loaded onto an AKTA Express Purification system with a Protein G column and PBS as the running buffer. The bound material was eluted with 0.1 M glycine/HCl pH 2.7 and pH adjusted to ~pH 7.0 with 2M Tris/HCl pH 8.5. The eluted material was then concentrated using 10 kDa molecular weight concentrators and the resulting concentrate was loaded onto a Superdex column (GE Healthcare) for gel filtration with PBS as the running buffer. Individual elution peaks were collected and analyzed by size exclusion HPLC to determine the monomeric fraction. The final monomeric protein was concentrated to 5 mg/ml in PBS and stored at 4° C.

SDS-PAGE Analysis of Protein-G Purified, CHOS Expressed Monomeric Fraction of Fab-1×dsscFv-1×scFv and Fab-2×dsscFv Formats Samples (2 µg) were diluted with PBS to a volume of 9.75 µl to which 3.75 µl 4×LDS sample buffer and 1.5 µl 100 mM N-ethylmaleimide (non-reduced samples) or 1.5 µl 10× NuPAGE reducing agent (reduced samples) was added. The samples were vortexed, incubated at 70° C. for 10 minutes, cooled and centrifuged at 12500 rpm for 30 seconds. The prepared samples were loaded onto a 4-20% acrylamide Tris/Glycine SDS gel and run for ~100 minutes at 125V, constant voltage. Mark12 (Life Technologies) molecular weight ladder was used. The gels were stained with Instant Blue protein stain (Expedeon) and destained with distilled water.

The expected band sizes after reducing and non-reducing SDS-PAGE are indicated in Table 9.

TABLE 9

Expected band sizes after SDS-PAGE (kDa)
(H = heavy chain, L = light chain, +/− reducing agent)

| | −Red | +Red | | −Red | +Red |
|---|---|---|---|---|---|
| Fab-1dsscFv, 1x scFv | ~100 | H~50 L~50 | Fab-2dsscFv | ~100 | H~50 L~50 |

For all proteins, the non-reducing gel was expected to show a band at ~100 kDa, whilst the reducing gels were expected to show a doublet at ~50 kDa with equal staining in the both bands.

For all Fab-1×dsscFv-1×scFv and Fab-2×dsscFv proteins, the reducing SDS-PAGE gels showed banding patterns which indicated that the constructs were monomeric and expressed correctly in terms of both migration position and staining intensity with a doublet at ~50 kDa (FIG. 8B, D). The additional uppermost minor band is consistent with non-reduced full-length protein (FIG. 8B, D). For all proteins, the non-reducing gel showed a band at ~100 kDa, indicative of the full-length protein (FIG. 8A, a). The minor bands at ~50 kDa on the non-reducing gel (FIG. 8A, b) may be consistent with incomplete disulphide bond formation between the heavy and light chain in the Fab region.

Figure 9:
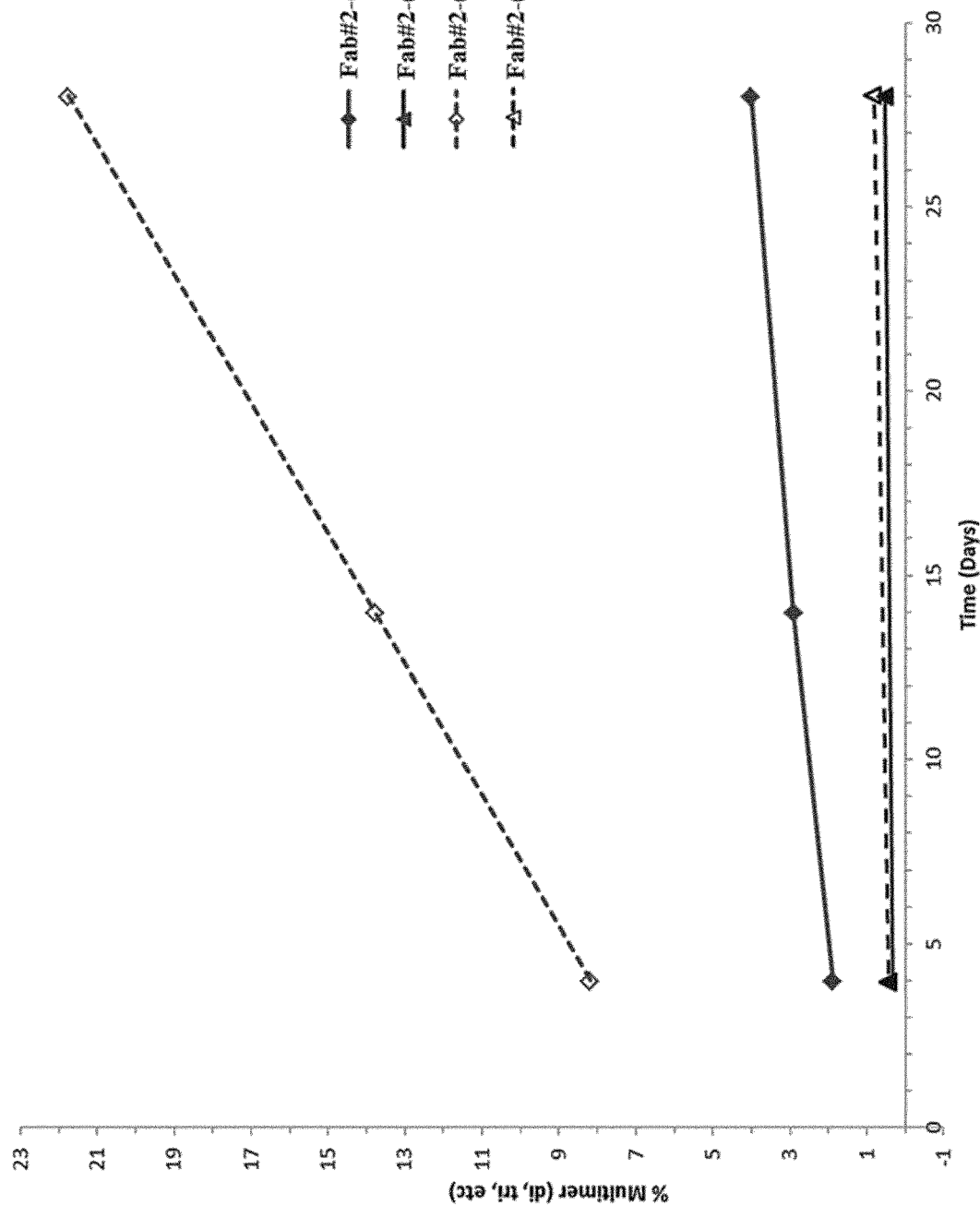
FIG. 9 shows G3000 SE-HPLC time-course analysis of monomeric Fab-1×dsscFv-1×scFv and Fab-2×dsscFv formats

G3000 SE-HPLC Time-Course Analysis of Monomeric Fab-1×dsscFv-1×scFv and Fab-2×dsscFv Formats A 5 mg/ml of purified monomer of the antibody formats was stored at 4° C. in PBS and analyzed on day 4, day 14 and day 28 after purification. Samples were diluted in PBS to 10 µg and injected onto a TSK Gel G3000SWXL, 7.8×300 mm, column (Tosoh) and developed with an isocratic gradient of 200 mM phosphate pH 7.0 at 1 ml/min. Signal detection was by absorbance at 280 nm. The results are shown in FIG. 9. On day 4 post-purification, analysis of Fab-2×dsscFv indicated that the majority of the protein was monomeric at the start of the experiment (solid lines), and remained monomeric and stable over the time course, with <1% defined as multimers (dimers, trimers, higher orders and large aggregates). On the other hand, a higher occurrence of multimerisation was detected for Fab-1×dsscFv-1×scFv which was observed to increase linearly over time (dashed lines). Indeed, the prevalence of multimerisation appeared to be more pronounced with formats containing non-disulphide stabilized scFvs in the $V_L/V_H$ orientation. However, it is clear that formats that contain a scFv lacking the Fv disulphide are in dynamic equilibrium and more prone to multimerisation during storage than scFvs which are disulphide stabilized. Indeed, formats that contain scFvs that are both disulphide stabilized have been shown to remain monomeric even when the concentration of the protein in a given formulation is increased. This makes constructs where both scFvs contain an Fv disulphide ideally suitable for use in pharmaceutical preparations where the risk of forming higher orders of multimers or large aggregates during periods of storage critically needs to be insignificant.

Example 2

Fab-2×dsscFv (Bivalent with Two of the Same dsscFv)

Construction of Plasmids for Expression in Mammalian Cells

Plasmids for the expression of Fab #2-(HC)dsscFv #3, (LC)dsscFv #3 (see FIG. 4), were constructed by fusing dsscFv #3 to the C-terminus of the Km3 allotype human kappa constant region of the light chain #2 using the flexible linker SGGGGSGGGGS [also referred herein as S, 2×G4S] (SEQ ID NO: 2), or by fusing dsscFv #3 to the C-terminus of the, γ1 isotype human gamma-1 $CH_1$ constant region of the heavy chain #2 using the flexible linker SGGGGTGGGGS [also referred to herein as S, G4T, G4S] (SEQ ID NO: 1). Point mutations were introduced into the DNA sequences at selected residues in the framework region of both vL #3/vL #1 and vH #3/vH #1. The mutations (heavy chain G44C and light chain G100C) were introduced to create an interchain disulphide bond between the heavy and light chains of the Fv #3.

pND1 plasmid (Fab #2 Heavy-(SGGGGTGGGGS [SEQ ID NO: 1)-dsvH #3-(GGGGSGGGGSGGGGSGGGGS [SEQ ID NO: 68])-dsvL #3) [Plasmid i] was already available. The gene fragment encoding dsHLscFv #3 was excised from pND1 and fused to light chain #2 as detailed above to generate: Light #2-(SGGGGSGGGGS [SEQ ID NO: 2])-dsvH #3-(GGGGSGGGGSGGGGSGGGGS [SEQ ID NO: 68])-dsvL #3 [Plasmid j].

The Fab fusion formats were cloned into mammalian expression vectors under the control of the HCMV-MIE promoter and SV40E polyA sequence.

HEK293 Expression of Fab-2×dsscFv #3

HEK293 cells were transfected with the relevant plasmids using Invitrogen's 293fectin transfection reagent according to the manufacturer's instructions. Plasmids were mixed as shown in Table 10 to express the protein:

TABLE 10

| Antibody Construct | Plasmids used |
| --- | --- |
| Fab#2-(HC)dsHLscFv#3, (LC)dsHLscFv#3 | 1. Plasmid j<br>2. Plasmid i |

The ratio of the plasmids used for the transfections was 1:1. A total of 50 μg plasmid DNA was incubated with 125 μl 293fectin+4.25 ml Optimem media for 20 mins at RT. The mixture was then added to 50 ml HEK293 cells in suspension at 1×10⁶ cells/ml and incubated with shaking at 37° C. Supernatants were harvested on day 10 by centrifugation at 1500 g to remove cells and the supernatant was passed through a 0.22 μm filter. Expression level was determined by Protein-G HPLC. Table 11 shows the results of the Protein-G HPLC assay. The level of expression was 20 μg/ml.

TABLE 11

| Antibody Construct | Expression level (μg/ml) |
| --- | --- |
| Fab#2(HC)dsHLscFv#3, (LC)dsHLscFv#3 | 20 |

Purification of HEK293 Expressed Fab-2×dsscFv #3

The ~50 ml HEK293 supernatants were concentrated ~25 fold to ~2 ml using 30 kDa molecular weight cut off centrifugation concentrators. The concentrated supernatants were purified and further concentrated and buffer exchanged into PBS pH 7.4 using 30 kDa molecular weight cut off centrifugation concentrators.

SDS-PAGE Analysis of Protein-G Purified, HEK293 Expressed Fab-2×dsscFv #3

Samples (2 μg) were diluted with PBS to a volume of 9.75 μl to which 3.75 μl 4×LDS sample buffer and 1.5 μl 100 mM N-ethylmaleimide (non-reduced samples) or 1.5 μl 10× NuPAGE reducing agent (reduced samples) was added. The samples were vortexed, incubated at 70° C. for 10 minutes, cooled and centrifuged at 12500 rpm for 30 seconds. The prepared samples were loaded onto a 4-20% acrylamide Tris/Glycine SDS gel and run for ~100 minutes at 125V, constant voltage. SeeBluePlus2 (Life Technologies) molecular weight ladder was used. The gels were stained with Instant Blue protein stain (Expedeon) and destained with distilled water. The expected band sizes after reducing and non-reducing SDS-PAGE are indicated in Table 12.

TABLE 12

| Expected band sizes after SDS-PAGE (kDa) (H = heavy chain, L = light chain, +/− reducing agent) | | |
| --- | --- | --- |
| | −Red | +Red |
| Fab-2xdsscFv#3 | ~100 | H~50 L~50 |

The non-reducing gel was expected to show a band at ~100 kDa, whilst the reducing gel was expected to show a doublet at ~50 kDa with equal staining in both bands.

The reducing SDS-PAGE gels showed banding patterns which indicated that the constructs were being expressed correctly in terms of both migration position and staining intensity with a doublet at ~50 kDa (FIG. 4B), however some additional minor species were also observed possibly owing to sub-optimal purification scheme as opposed to the standard Protein G-mediated purification method, which is typically used for purification of Fabs. Disulphide linked multimers are seen on the non-reducing gel (FIG. 4A), which disappear under reducing conditions (FIG. 4B).

S200 SE-HPLC Analysis of Purified, HEK293 Expressed Fab-2×dsscFv #3

10 μg purified protein samples (100 μl of 0.1 mg/ml stock diluted in PBS) were injected onto a Superdex 200 10/300 GL Tricorn column (GE Healthcare) 3 days post-purification and developed with an isocratic gradient of PBS pH 7.4 at 1 ml/min, with continuous detection by absorbance at 280 nm. The results are shown in FIG. 5. As can be seen from FIG. 5, after purification, the Fab-2×dsscFv #3 format was 81% monomer.

Example 3

Fab-(HC)dsscFv-(LC)dsFv

Construction of Fab #2-(HC)dsscFv #3-(LC)dsscFv #1 and Fab #2-(HC)dsscFv #3-(LC)dsFv #1 (LC-vL Linked) Plasmids for Expression in Mammalian Cells The Fab #2 fusion proteins for the expression of Fab #2-(HC)dsscFv #3-(LC)dsscFv #1 and Fab #2-(HC)dsscFv #3-(LC)dsFv #1 (LC-vL linked) (see FIG. 6), were constructed by fusing either dsscFv #1 (dsvH-4×G4S-dsvL) or dsvL #1 to the C-terminus of the Km3 allotype human kappa constant region of the light chain #2 using the flexible linker SGGGGSGGGGSGGGGS (SEQ ID NO: 69) to generate:

```
Light#2-(SGGGGSGGGGSGGGGS [SEQ ID NO: 69])-
dsscFv#1 [Plasmid b]
and

Light#2-(SGGGGSGGGGSGGGGS [SEQ ID NO: 69])-
dsvL#1 [Plasmid c];
``` and by fusing HLdsscFv #3 (dsvH-4×G4S-dsvL) to the C-terminus of the, γ1 isotype human gamma-1 CH1 constant region of the heavy chain #2 using the flexible linker SGGGGSGGGGTGGGGS (SEQ ID NO: 70) to generate:

```
Heavy#2-(SGGGGSGGGGTGGGGS [SEQ ID NO: 70])-
dsscFv#3 [Plasmid a].
```

Point mutations (heavy chain G44C and light chain G100C) were introduced into the DNA sequences at selected residues in the framework region of vL #3, vH #3, vL #1 and vH #1 to create an interchain disulphide bond between the heavy and light chains of the Fv #3 and Fv #1. Heavy and light chain Fab-fusion genes were cloned into mammalian expression vectors under the control of the HCMV-MIE promoter and SV40E polyA sequence. Genes encoding:

```
Heavy#2-(SGGGGSGGGGTGGGGS [SEQ ID NO: 70])-
dsscFv#3 [Plasmid a]
and dsvH#1 free domain [Plasmid d]
``` were manufactured chemically and individually cloned into mammalian expression vectors under the control of the HCMV-MIE promoter and SV40E polyA sequence.

The genes encoding dsscFv #1 and dsvL #1 were manufactured chemically and fused to the C-terminal of light chain #2 to create:

```
Light#2-(SGGGGSGGGGSGGGGS [SEQ ID NO: 69])-
dsscFv#1 [Plasmid b]
and

Light#2-(SGGGGSGGGGSGGGGS [SEQ ID NO: 69])-
dsvL#1 [Plasmid c]
``` and the entire constructs were cloned into a mammalian expression vector under the control of the HCMV-MIE promoter and SV40E polyA sequence.

HEK293 Expression of:
Fab #2-(HC)dsscFv #3-(LC)dsscFv #1 and
Fab #2-(HC)dsscFv #3-(LC)dsFv #1 (LC-vL linked)

HEK293 cells were transfected with the relevant plasmids using Invitrogen's 293fectin transfection reagent according to the manufacturer's instructions. Plasmids were mixed as follows to express the different constructs as shown in Table 13 below:

TABLE 13

| Antibody Construct | Plasmids used |
| --- | --- |
| Fab#2-(HC)dsscFv#3-(LC)dsscFv#1 | 1. Plasmid a |
|  | 2. Plasmid b |
| Fab#2-(HC)dsscFv#3-(LC)dsFv#1 (LC-vL linked) | 1. Plasmid a |
|  | 2. Plasmid c |
|  | 3. Plasmid d |

For the 2 plasmid combination, the ratio of the plasmids used for the transfections was 1:1, whereas for the 3 plasmid combinations the ratio was 1:1:1. A total of 50 μg plasmid DNA was incubated with 125 μl 293fectin+4.25 ml Optimem media for 20 mins at RT. The mixture was then added to 50 ml HEK293 cells in suspension at 1×10$^6$ cells/ml and incubated with shaking at 37° C. Supernatants were harvested on day 10 by centrifugation at 1500 g to remove cells and the supernatant was passed through a 0.22 μm filter. Expression level was determined by Protein-G HPLC.

The results are shown in Table 14. As can be seen, the levels of expression of both constructs were comparable to each other (16-18 μg/ml). There have been reports in the literature that the expression of Fv regions that lack either a linker between the vL and vH or a dimerisation motif to bring the vL and vH together have substantially lower expression levels than linked Fvs. Surprisingly, this is not observed in this data where there was no significant difference observed between the expression level of each type of construct.

TABLE 14

| Construct | Expression level (μg/ml) |
| --- | --- |
| Fab#2-(HC)dsscFv#3-(LC)dsscFv#1 | 18 |
| Fab#2-(HC)dsscFv#3-(LC)dsFv#1 (LC-vL linked) | 16 |

Protein-G Purification of HEK293 Expressed Fab #2-(HC)dsscFv #3-(LC)dsscFv #1 and Fab #2-(HC)dsscFv #3-(LC)dsFv #1 (LC-vL Linked)

The ~50 ml HEK293 supernatants were concentrated ~25 fold to ~2 ml using 10 kDa molecular weight cut off centrifugation concentrators. The concentrated supernatants were applied to a 1 ml HiTrap Protein-G FF column (GE Healthcare) equilibrated in 20 mM phosphate, 40 mM NaCl pH 7.4. The column was washed with 20 mM phosphate, 40 mM NaCl pH 7.4 and the bound material was eluted with 0.1M glycine/HCl pH 2.7. The elution peak was collected and pH adjusted to ~pH 7.0 with 2M Tris/HCl pH 8.5. The pH adjusted elutions were concentrated and buffer exchanged into PBS pH 7.4 using 10 kDa molecular weight cut off centrifugation concentrators.

SDS-PAGE Analysis of Protein-G Purified, HEK293 Expressed Fab #2-(HC)dsscFv #3-(LC) dsscFv #1 and Fab #2-(HC)dsscFv #3-(LC)dsFv #1 (LC-vL Linked)

Samples (2 μg) were diluted with PBS to a volume of 9.75 μl to which 3.75 μl 4×LDS sample buffer and 1.5 μl 100 mM N-ethylmaleimide (non-reduced samples) or 1.5 μl 10× NuPAGE reducing agent (reduced samples) was added. The samples were vortexed, incubated at 70° C. for 10 minutes, cooled and centrifuged at 12500 rpm for 30 seconds. The prepared samples were loaded onto a 4-20% acrylamide Tris/Glycine SDS gel and run for ~100 minutes at 125V, constant voltage. SeeBluePlus2 (Life Technologies) molecular weight ladder was used. The gels were stained with Instant Blue protein stain (Expedeon) and destained with distilled water.

The results are shown in FIG. 6. For Fab #2-(HC)dsscFv #3-(LC)dsscFv #1, the non-reducing gel was expected to show a band at ~100 kDa, whilst the reducing gel was expected to show a doublet at ~50 kDa with roughly equal staining in both bands. For Fab #2-(HC)dsscFv #3-(LC)dsFv #1 (LC-vL linked), the non-reducing gel was expected to show a band at ~100 kDa, whilst the reducing gel was expected to show 3 bands at ~50, ~36 and ~13 kDa with staining roughly in the ratio 3:2:1 upper to lower band.

The reducing SDS-PAGE gels showed banding patterns which indicated that the constructs were being expressed correctly in terms of both migration position and staining intensity. Non-reducing SDS-PAGE gels showed significant banding patterns >200 kDa for Fab-2×dsscFv that were consistent with multimerisation (FIG. 6A, lane 2) but fewer high molecular weight species were observed in the Fab-dsscFv-dsFv sample (FIG. 6B, lane 2).

G3000 SE-HPLC Analysis of Protein-G Purified, HEK293 Expressed, Fab #2-(HC)dsscFv #3-(LC)dsscFv #1 and Fab #2-(HC)dsscFv #3-(LC)dsFv #1 (LC-vL Linked)

10 µg purified protein samples (100 µl of 0.1 mg/ml stock diluted in PBS) were injected onto a TSK Gel G3000SWXL, 7.8×300 mm, column (Tosoh) 3 days post-purification and developed with an isocratic gradient of 200 mM phosphate pH 7.0 at 1 ml/min. Signal detection was by absorbance at 280 nm.

The results are shown in FIG. 7. After Protein-G purification, the Fab #2-(HC)dsscFv #3-(LC)dsFv #1 (LC-vL linked) was 91% monomer, whereas the Fab #2-(HC)dsscFv #3-(LC)dsscFv #1 was 30% monomer.

dsscFv #1 is known to be particularly prone to multimerisation. Given that multimers are physically joined by the dsscFv linker (the vL #1 or vH #1 is paired with vH #1 or vL #1 from a different polypeptide chain), by replacing dsscFv #1 with dsFv #1 (which does not comprise a scFv linker), there was a significant increase in the percentage monomer obtained.

The skilled person will thus appreciate that, depending on the propensity of the dsscFv to multimerise, in some instances it would be advantageous to use a dsFv instead of a dsscFv.

Example 4

Biacore Affinity and Demonstration of Simultaneous Binding of Antigen Targets

The binding affinities and kinetic parameters for the interactions of Fab #2-(HC)dsHLscFv #3 (LC)dsHLscFv #4 were determined by surface plasmon resonance (SPR) conducted on a BIAcore T100 or a BIAcore 3000 using CM5 sensor chips (GE Healthcare Bio-Sciences AB) and HBS-EP (10 mM HEPES (pH 7.4), 150 mM NaCl, 3 mM EDTA, 0.05% v/v surfactant P20) running buffer. All experiments were performed at 25° C. The antibody samples were captured to the sensor chip surface using either a human F(ab')$_2$-specific goat Fab (Jackson ImmunoResearch) or an in-house generated anti human CH$_1$ monoclonal antibody. Covalent immobilization of the capture antibody was achieved by standard amine coupling chemistry to a level of 6000-7000 response units (RU). Antigen #2, #3 or #4 was titrated separately over the captured antibody. Each assay cycle consisted of firstly capturing the antibody sample using a 1 min injection, before an association phase consisting of a 3 min injection of antigen, after which dissociation was monitored for 10 min. After each cycle, the capture surface was regenerated with 2×1 min injections of 40 mM HCl followed by 30 s of 5 mM NaOH. The flow rates used were 10 µl min$^{-1}$ for capture, 30 µl min$^{-1}$ for association and dissociation phases, and 10 µl min$^{-1}$ for regeneration. Kinetic parameters were determined by simultaneous global-fitting of the resulting sensorgrams to a standard 1:1 binding model using BIAcore T100 Evaluation software v2.0.1 or BIAcore 3000 BIAevaluation v3.2. The results are shown in Table 15. The antibody showed expected affinities within the pM-nM range for the antigens tested.

TABLE 15

| Analyte | ka (1/Ms) | kd (1/s) | KD (M) | KD (pM) |
|---|---|---|---|---|
| Antigen #2 | 5.06E+06 | 3.80E−05 | 7.51E−12 | 7.51 |
| Antigen #3 | 5.54E+06 | 6.43E−05 | 1.16E−11 | 11.6 |
| Antigen #4 | 7.75E+04 | 1.35E−04 | 1.74E−09 | 1740 |

The potential for of Fab #2-(HC)dsHLscFv #3 (LC) dsHLscFv #4 to bind simultaneously to all 3 antigens was assessed by capturing the tri-specific antibody to the sensor chip via immobilized anti-human IgG-F(ab')$_2$. Each antigen or a mixed solution of antigen #2, #3 and #4 was titrated over the captured antibody in 3 min injections. The binding responses observed for the independent injections and combined responses are shown in Table 16. The binding response for the combined antigen #2/#3/#4 solution was equivalent to the sum of the responses of the independent injections. This confirms that of Fab #2-(HC)dsHLscFv #3 (LC)dsHLscFv #4 is capable of simultaneous binding to all 3 antigens tested.

TABLE 16

| Analyte | Binding (RU) |
|---|---|
| Antigen #2 | 58 |
| Antigen #3 | 38 |
| Antigen #4 | 47 |
| Antigens #2 + #3 + #4 | 130 (143) |

Example 5

Comparison of Monomeric Yield Between Fab-2×scFv and Fab-2×dsscFv Formats

EXpiHEK cells were transfected with the relevant plasmids by electroporation methods at 50 ml scale. Plasmids were mixed as shown in Table 17 to express the protein. Cultures were grown in ExpiHEK expression medium and incubated at 37° C. with 8% CO$_2$ at 120 rpm for 16-18 h, prior to addition of enhancer 1 and 2. The cultures were subsequently incubated for a further 4 days at 37° C. Culture supernatants were harvested by centrifugation and 0.22 µm filter sterilized. Expression titres were measured by Protein G HPLC (Table 18).

TABLE 17

| Antibody Construct | Plasmids used |
|---|---|
| Fab#4-(LC)HLscFv#5, (HC)HLscFv#6 | 1. Plasmid k1<br>2. Plasmid l1 |
| Fab#4-(LC)dsHLscFv#5, (HC)dsHLscFv#6 | 1. Plasmid k2<br>2. Plasmid l2 |
| Fab#4-(LC)HLscFv#7, (HC)HLscFv#8 | 1. Plasmid m1<br>2. Plasmid n1 |
| Fab#4-(LC)dsHLscFv#7, (HC)dsHLscFv#8 | 1. Plasmid m2<br>2. Plasmid n2 |
| Fab#4-(LC) HLscFv#9, (HC)LHscFv#10 | 1. Plasmid o1<br>2. Plasmid p1 |
| Fab#4-(LC)dsHLscFv#9, (HC)dsLHscFv#10 | 1. Plasmid o2<br>2. Plasmid p2 |
| Fab#4-(LC)HLscFv#7, (HC)LHscFv#10 | 4. Plasmid q1<br>5. Plasmid r1 |

TABLE 17-continued

| Antibody Construct | Plasmids used |
| --- | --- |
| Fab#4-(LC)dsHLscFv#7, (HC)dsLHscFv#10 | 1. Plasmid q2<br>2. Plasmid r2 |

TABLE 18

| Antibody Construct | Expression (μg/ml) |
| --- | --- |
| Fab#4-(LC)HLscFv#5, (HC)HLscFv#6 | 62 |
| Fab#4-(LC)dsHLscFv#5, (HC)dsHLscFv#6 | 31 |
| Fab#4-(LC)HLscFv#7, (HC)HLscFv#8 | 195 |
| Fab#4-(LC)dsHLscFv#7, (HC)dsHLscFv#8 | 34 |
| Fab#4-(LC) HLscFv#9, (HC)LHscFv#10 | 298 |
| Fab#4-(LC)dsHLscFv#9, (HC)dsLHscFv#10 | 55 |
| Fab#4-(LC)HLscFv#7, (HC)LHscFv#10 | 226 |
| Fab#4-(LC)dsHLscFv#7, (HC)dsLHscFv#10 | 58 |

Protein-G Purification of EXPiHEK Expressed Fab-2×scFvFv and Fab-2×dsscFv Formats Supernatants were concentrated ~25 fold to ~2 ml using a 10 kDa molecular weight cut off concentrators. The concentrated supernatants were purified by protein G HPLC using phosphate buffer pH 7.4. The bound material was eluted with 0.1 M glycine/HCl pH 2.7 and pH adjusted to ~pH 7.0 with 2M Tris/HCl pH 8.5. The eluted material was concentrated using 10 kDa molecular weight concentrators and buffer exchanged into PBS. The purified protein was concentrated to ~4-5 mg/ml in PBS and stored at 4° C.

SDS-PAGE Analysis of Protein-G Purified, EXPiHEK Expressed Fab-2×scFv and Fab-2×dsscFv Formats Samples (2 μg) were diluted with PBS to a volume of 9.75 μl to which 3.75 μl 4×LDS sample buffer and 1.5 μl 100 mM N-ethylmaleimide (non-reduced samples) or 1.5 μl 10× NuPAGE reducing agent (reduced samples) was added. The samples were vortexed, incubated at 70° C. for 10 minutes, cooled and centrifuged at 12500 rpm for 30 seconds. The prepared samples were loaded onto a 4-20% acrylamide Tris/Glycine SDS gel and run for ~100 minutes at 125V, constant voltage. Seeblue2 (Life Technologies) molecular weight ladder was used. The gels were stained with Instant Blue protein stain (Expedeon) and destained with distilled water.

The expected band sizes after reducing and non-reducing SDS-PAGE are indicated in Table 19.

TABLE 19

| Expected band sizes after SDS-PAGE (kDa) (H = heavy chain, L = light chain, +/− reducing agent) | | | | | |
| --- | --- | --- | --- | --- | --- |
| | −Red | +Red | | −Red | +Red |
| Fab-2xscFv | ~100 | H~50 L~50 | Fab-2xdsscFv | ~100 | H~50 L~50 |

For all proteins, the non-reducing gel was expected to show a band at ~100 kDa, whilst the reducing gels were expected to show a doublet at ~50 kDa with equal staining in the both bands.

For all Fab-2×scFv and Fab-2×dsscFv proteins, the reducing SDS-PAGE gels showed banding patterns which indicated that the constructs expressed correctly in terms of both migration position and staining intensity with a doublet at ~50 kDa (FIG. 10B,a). The additional uppermost minor band is consistent with non-reduced full-length protein (FIG. 10B,b). For all proteins, the non-reducing gel showed a band at ~130 kDa, indicative of the full-length protein (FIG. 10A,a). The bands at ~50 kDa on the non-reducing gel (FIG. 10A, b) may be consistent with incomplete disulphide bond formation between the heavy and light chain in the Fab region.

G3000 SE-HPLC Analysis of Fab-2×scFv and Fab-2×dsscFv Formats

Purified antibody proteins at ~5 mg/ml were stored at 4° C. in PBS for 24 h prior to analysis. Samples equivalent to a concentration of 25 μg were injected onto a TSK Gel G3000SWXL, 7.8×300 mm, column (Tosoh) and developed with an isocratic gradient of 200 mM phosphate pH 7.0 at 1 ml/min. Signal detection was by absorbance at 280 nm. The results are shown in Table 20. Analysis indicated that all Fab-2×dsscFv proteins were >90% monomeric. On the other hand, a higher occurrence of multimerisation was detected for all Fab-2×scFv. It is clear that formats that contain scFvs with an Fv disulphide are more monomeric compared to scFvs lacking the Fv disulphide. This indicates a preference for using formats with scFvs that contain Fv disulphides in terms of selecting therapeutic molecules with stable qualities and also attributes that would be advantageous in a manufacturing process.

TABLE 20

| Format | % monomer |
| --- | --- |
| Fab#4-(LC)HLscFv#5, (HC)HLscFv#6 | 51.3 |
| Fab#4-(LC)dsHLscFv#5, (HC)dsHLscFv#6 | 96.8 |
| Fab#4-(LC)HLscFv#7, (HC)HLscFv#8 | 80.8 |
| Fab#4-(LC)dsHLscFv#7, (HC)dsHLscFv#8 | 98.8 |
| Fab#4-(LC) HLscFv#9, (HC)LHscFv#10 | 84.9 |
| Fab#4-(LC)dsHLscFv#9, (HC)dsLHscFv#10 | 94.3 |
| Fab#4-(LC)HLscFv#7, (HC)LHscFv#10 | 53.2 |
| Fab#4-(LC)dsHLscFv#7, (HC)dsLHscFv#10 | 90.8 |

The invention claimed is:

1. A multi-specific antibody molecule comprising
a) a polypeptide chain of formula (I):

$V_H$—$CH_1$—X—$V_1$; and b) a polypeptide chain of formula (II):

$V_L$—$C_L$—Y—$V_2$;

wherein:
$V_H$ represents a heavy chain variable domain;
$CH_1$ represents a domain of a heavy chain constant region;
X represents a bond or linker;
Y represents a bond or linker;
$V_1$ represents a dsscFv;
$V_L$ represents a light chain variable domain;
$C_L$ represents a domain from a light chain constant region;
$V_2$ represents a dsscFv.

2. The multi-specific antibody molecule according to claim 1, wherein X is a linker.

3. The multi-specific antibody molecule according to claim 1, wherein Y is a linker.

4. The multi-specific antibody molecule according to claim 1, wherein the light chain variable domain of $V_1$ is attached to X.

5. The multi-specific antibody molecule according to claim 1, wherein the light chain variable domain of $V_2$ is attached to Y.

6. The multi-specific antibody molecule according to claim 1, wherein the light chain and heavy chain variable domains of $V_1$ and/or the light chain and heavy chain variable domains of $V_2$ are linked by a disulfide bond between two engineered cysteine residues.

7. The multi-specific antibody molecule according to claim 1, wherein the heavy chain and light chain variable domains of $V_1$ and/or $V_2$ are linked by a disulfide bond between two engineered cysteine residues, wherein the position of the pair of engineered cysteine residues is selected from the group comprising or consisting of: $V_H37$ and $V_L95$, $V_H44$ and $V_L100$, $V_H44$ and $V_L105$, $V_H45$ and $V_L87$, $V_H100$ and $V_L50$, $V_H100b$ and $V_L49$, $V_H98$ and $V_L46$, $V_H101$ and $V_L46$, $V_H105$ and $V_L43$ and $V_H106$ and $V_L57$, wherein the $V_H$ and $V_L$ values are independently selected within a given $V_1$ or $V_2$, wherein the numbering is according to Kabat.

8. The multi-specific antibody molecule according to claim 7, wherein the position of the pair of engineered cysteine residues is $V_H44$ and $V_L100$, wherein the numbering is according to Kabat.

9. The multi-specific antibody molecule according to claim 1, wherein X is a peptide linker.

10. The multi-specific antibody molecule according to claim 1, wherein Y is a peptide linker.

11. The multi-specific antibody molecule according to claim 1 which is tri-specific.

12. The tri-specific antibody molecule according to claim 11, wherein VH/VL, V1 and V2 are each binding domains that bind to different antigens.

13. A pharmaceutical composition comprising a multi-specific antibody molecule according to claim 1 and at least one excipient.

14. The multi-specific antibody molecule according to claim 9, wherein X is a peptide linker selected from SEQ ID NO: 1, 2, 69, or 70.

15. The multi-specific antibody molecule according to claim 10, wherein Y is a peptide linker selected from SEQ ID NO: 1, 2, 69, or 70.

16. A formulation comprising the multi-specific antibody molecule of claim 1, wherein at least 98% of the multi-specific antibody molecule in the formulation is present in monomeric form after storage for 28 days at 4° C.

17. The multi-specific antibody of claim 1, wherein $V_1$ and $V_2$ are specific for two different antigens.

18. A multi-specific antibody molecule consisting of:
c) a polypeptide chain of formula (I):

$V_H$—$CH_1$—X—$V_1$; and d) a polypeptide chain of formula (II):

$V_L$—$C_L$—Y—$V_2$;

wherein:
$V_H$ represents a heavy chain variable domain;
$CH_1$ represents a domain of a heavy chain constant region;
X represents a bond or linker;
Y represents a bond or linker;
$V_1$ represents a dsscFv;
$V_L$ represents a light chain variable domain that binds the first antigen;
$C_L$ represents a domain from a light chain constant region;
$V_2$ represents a dsscFv; and
wherein V1 and V2 are specific for two different antigens.

19. A formulation comprising a multi-specific antibody molecule comprising:
e) a polypeptide chain of formula (I):

$V_H$—$CH_1$—X—$V_1$; and f) a polypeptide chain of formula (II):

$V_L$—$C_L$—Y—$V_2$;

wherein:
$V_H$ represents a heavy chain variable domain;
$CH_1$ represents a domain of a heavy chain constant region;
X represents a bond or linker;
Y represents a bond or linker;
$V_1$ represents a dsscFv;
$V_L$ represents a light chain variable domain;
$C_L$ represents a domain from a light chain constant region;
$V_2$ represents a dsscFv; and
wherein at least 98% of the multi-specific antibody molecule in the formulation is present in monomeric form after storage for 28 days at 4° C.

20. The multi-specific antibody molecule of claim 1, wherein only one of $V_H/V_L$, $V_1$ or $V_2$ has specificity for a serum carrier protein.

21. The multi-specific antibody molecule of claim 20, wherein the serum carrier protein is human serum albumin and wherein said $V_H/V_L$ or $V_1$ or $V_2$ having specificity for a serum carrier protein forms an albumin binding site.

22. The multi-specific antibody molecule of claim 21, wherein the albumin binding site comprises SEQ ID NO: 71 for CDRH1, SEQ ID NO: 72 for CDRH2, SEQ ID NO: 73 for CDRH3, SEQ ID NO: 74 for CDRL1, SEQ ID NO: 75 for CDRL2 and SEQ ID NO: 76 for CDRL3; or a heavy chain variable domain selected from SEQ ID NO: 77 and SEQ ID NO: 78 and a light chain variable domain selected from SEQ ID NO: 79 and SEQ ID NO: 80.

23. The multi-specific antibody molecule of claim 22, wherein $V_1$ comprises the albumin binding site.

24. The multi-specific antibody molecule of claim 22, wherein $V_2$ comprises the albumin binding site.

25. The multi-specific antibody molecule of claim 1, wherein the heavy chain variable domain of $V_1$ is attached to X.

26. The multi-specific antibody molecule of claim 1, wherein the heavy chain variable domain of $V_2$ is attached to Y.

* * * * *